(12) United States Patent
Iswanto et al.

(10) Patent No.: US 12,238,489 B2
(45) Date of Patent: Feb. 25, 2025

(54) PATIENT MONITOR ALARM SPEAKER ANALYZER

(71) Applicant: MASIMO CORPORATION, Irvine, CA (US)

(72) Inventors: Joy Iswanto, Irvine, CA (US); Bilal Muhsin, San Clemente, CA (US); Raul Jimenez, Laguna Hills, CA (US)

(73) Assignee: Masimo Corporation, Irvine, CA (US)

( * ) Notice: Subject to any disclaimer, the term of this patent is extended or adjusted under 35 U.S.C. 154(b) by 5 days.

(21) Appl. No.: 18/475,723

(22) Filed: Sep. 27, 2023

(65) Prior Publication Data

US 2024/0171920 A1    May 23, 2024

Related U.S. Application Data

(63) Continuation of application No. 17/387,513, filed on Jul. 28, 2021, now Pat. No. 11,812,229, which is a
(Continued)

(51) Int. Cl.
*H04R 29/00*      (2006.01)
*A61B 5/00*      (2006.01)
(Continued)

(52) U.S. Cl.
CPC ....... *H04R 29/001* (2013.01); *A61B 5/14551* (2013.01); *A61B 5/7405* (2013.01);
(Continued)

(58) Field of Classification Search
CPC .... H04R 29/00; H04R 29/001; H04R 29/004; H04R 3/00; H04R 3/005; H04R 3/004;
(Continued)

(56) References Cited

U.S. PATENT DOCUMENTS

| | | | |
|---|---|---|---|
| 4,745,398 | A | 5/1988 | Abel et al. |
| 4,960,128 | A | 10/1990 | Gordon et al. |

(Continued)

OTHER PUBLICATIONS

US 2024/0016391 A1, 01/2024, Lapotko et al. (withdrawn)
(Continued)

*Primary Examiner* — Ahmad F. Matar
*Assistant Examiner* — Sabrina Diaz
(74) *Attorney, Agent, or Firm* — Knobbe, Martens, Olson & Bear, LLP

(57) ABSTRACT

A patient monitor can diagnose whether its speaker is blocked, malfunctioning, or at a volume that is too low. For example, the monitor can include a processor that can diagnose the speaker by recording a microphone input signal. The processor can compare the microphone input signal to an expected alarm signal that should be output by the speaker. If the two do not match or reasonably correspond to one another, then the processor may increase the volume of the alarm to determine whether doing so can overcome an obstruction, noise, or potential malfunction. The microphone can again detect the speaker output, and the processor can again make another comparison or analysis of the input with the speaker output. If the speaker output as detected via the microphone is still insufficiently loud, then the patient monitor may output an indication that the speaker has a problem.

22 Claims, 15 Drawing Sheets

Related U.S. Application Data continuation of application No. 16/920,604, filed on Jul. 3, 2020, now Pat. No. 11,082,786, which is a continuation of application No. 16/505,142, filed on Jul. 8, 2019, now Pat. No. 10,779,098.

(60) Provisional application No. 62/696,208, filed on Jul. 10, 2018, provisional application No. 62/745,096, filed on Oct. 12, 2018.

(51) Int. Cl.
| | |
|---|---|
| *A61B 5/1455* | (2006.01) |
| *G06F 3/16* | (2006.01) |
| *G08B 3/10* | (2006.01) |
| *G08B 29/10* | (2006.01) |
| *G10L 25/18* | (2013.01) |
| *G10L 25/51* | (2013.01) |
| *H04R 3/00* | (2006.01) |
| *H05K 5/02* | (2006.01) |
| *H05K 5/03* | (2006.01) |
| *G06F 3/04817* | (2022.01) |

(52) U.S. Cl.
CPC .............. *A61B 5/746* (2013.01); *G06F 3/165* (2013.01); *G08B 3/10* (2013.01); *G08B 29/10* (2013.01); *G10L 25/18* (2013.01); *G10L 25/51* (2013.01); *H04R 3/00* (2013.01); *H05K 5/0213* (2013.01); *H05K 5/03* (2013.01); *G06F 3/04817* (2013.01); *H04R 2430/01* (2013.01)

(58) Field of Classification Search
CPC ...... H04R 3/12; H04R 2430/01; H04R 27/00; A61B 5/14551; A61B 5/7405; A61B 5/746; G01H 3/14; G06F 3/165; G06F 3/04817; G08B 3/10; G08B 29/10; G10L 25/18; G10L 25/51; H04N 11/00; H04S 7/40; H04S 7/301; H03G 9/005; H03G 9/025; H03G 3/24
USPC ...................................................... 381/56–59
See application file for complete search history.

(56) References Cited

U.S. PATENT DOCUMENTS

| | | |
|---|---|---|
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| 5,345,510 A | 9/1994 | Singhi et al. |
| 5,377,676 A | 1/1995 | Vari et al. |
| 5,431,170 A | 7/1995 | Mathews |
| 5,436,499 A | 7/1995 | Namavar et al. |
| 5,452,717 A | 9/1995 | Branigan et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,558,065 A | 12/1996 | Tanaka et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,652,566 A | 7/1997 | Lambert |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |

(56) References Cited

U.S. PATENT DOCUMENTS

| | | |
|---|---|---|
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Ai-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al i et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |

(56) References Cited

U.S. PATENT DOCUMENTS

| | | |
|---|---|---|
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |

(56) References Cited

U.S. PATENT DOCUMENTS

| | | |
|---|---|---|
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |

(56) References Cited

U.S. PATENT DOCUMENTS

| | | |
|---|---|---|
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,509,817 B1 | 11/2016 | Peters |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |

(56) References Cited

U.S. PATENT DOCUMENTS

| | | |
|---|---|---|
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,433,776 B2 | 10/2019 | Al-Ali |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali |
| 10,456,038 B2 | 10/2019 | Lamego et al. |
| 10,463,284 B2 | 11/2019 | Al-Ali et al. |
| 10,463,340 B2 | 11/2019 | Telfort et al. |
| 10,470,695 B2 | 11/2019 | Al-Ali |
| 10,471,159 B1 | 11/2019 | Lapotko et al. |
| 10,478,107 B2 | 11/2019 | Kiani et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 * | 9/2020 | Iswanto .................. A61B 5/746 |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,082,786 B2 | 8/2021 | Iswanto et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |

(56) References Cited

U.S. PATENT DOCUMENTS

| | | |
|---|---|---|
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,812,229 B2 | 11/2023 | Iswanto et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| 12,004,869 B2 | 6/2024 | Kiani et al. |
| 12,014,328 B2 | 6/2024 | Wachman et al. |
| D1,036,293 S | 7/2024 | Al-Ali |
| 12,029,844 B2 | 7/2024 | Pauley et al. |
| 12,048,534 B2 | 7/2024 | Vo et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0106126 A1* | 5/2007 | Mannheimer ...... A61B 5/14551 600/323 |
| 2007/0109115 A1* | 5/2007 | Kiani ................ G08B 13/1966 340/507 |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0230733 A1 | 9/2011 | Al-Ali |
| 2012/0008269 A1 | 1/2012 | Gengler |
| 2012/0033375 A1 | 2/2012 | Madonna et al. |
| 2012/0123231 A1 | 5/2012 | O'Reilly |
| 2012/0162263 A1 | 6/2012 | Griffin et al. |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0135212 A1 | 5/2013 | Cheng et al. |
| 2013/0239960 A1* | 9/2013 | Bertinetti ............ E05B 17/2057 128/202.22 |
| 2013/0253334 A1 | 9/2013 | Al-Ali et al. |
| 2013/0296672 A1 | 11/2013 | O'Neil et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0257689 A1 | 9/2015 | Al-Ali et al. |
| 2015/0351697 A1 | 12/2015 | Weber et al. |
| 2015/0366507 A1 | 12/2015 | Blank |
| 2016/0029932 A1 | 2/2016 | Al-Ali |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0196388 A1 | 7/2016 | Lamego |
| 2016/0283681 A1 | 9/2016 | Falck et al. |
| 2016/0324488 A1 | 11/2016 | Olsen |
| 2016/0367173 A1 | 12/2016 | Dalvi et al. |
| 2017/0014083 A1 | 1/2017 | Diab et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0196464 A1 | 7/2017 | Jansen et al. |
| 2017/0196470 A1 | 7/2017 | Lamego et al. |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0289717 A1* | 10/2017 | Little ................... G06F 3/165 |
| 2017/0311891 A1 | 11/2017 | Kiani et al. |

(56) References Cited

U.S. PATENT DOCUMENTS

| | | |
|---|---|---|
| 2017/0340293 A1 | 11/2017 | Al-Ali et al. |
| 2017/0360310 A1 | 12/2017 | Kiani et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0132769 A1 | 5/2018 | Weber et al. |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153448 A1 | 6/2018 | Weber et al. |
| 2018/0168491 A1 | 6/2018 | Al-Ali et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242923 A1 | 8/2018 | Al-Ali et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0285094 A1 | 10/2018 | Housel et al. |
| 2018/0289325 A1 | 10/2018 | Poeze et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0001899 A1 | 1/2019 | Cadalora et al. |
| 2019/0015023 A1 | 1/2019 | Monfre |
| 2019/0029574 A1 | 1/2019 | Schurman et al. |
| 2019/0029578 A1 | 1/2019 | Al-Ali et al. |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0076028 A1 | 3/2019 | Al-Ali et al. |
| 2019/0082979 A1 | 3/2019 | Al-Ali et al. |
| 2019/0090760 A1 | 3/2019 | Kinast et al. |
| 2019/0090764 A1 | 3/2019 | Al-Ali |
| 2019/0117070 A1 | 4/2019 | Muhsin et al. |
| 2019/0117139 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0307377 A1 | 10/2019 | Perea et al. |
| 2019/0320906 A1 | 10/2019 | Olsen |
| 2019/0320959 A1 | 10/2019 | Al-Ali |
| 2019/0320988 A1 | 10/2019 | Ahmed et al. |
| 2019/0325722 A1 | 10/2019 | Kiani et al. |
| 2019/0350506 A1 | 11/2019 | Al-Ali |
| 2019/0357812 A1 | 11/2019 | Poeze et al. |
| 2019/0357813 A1 | 11/2019 | Poeze et al. |
| 2019/0357823 A1 | 11/2019 | Reichgott et al. |
| 2019/0357824 A1 | 11/2019 | Al-Ali |
| 2019/0358524 A1 | 11/2019 | Kiani |
| 2019/0365294 A1 | 12/2019 | Poeze et al. |
| 2019/0365295 A1 | 12/2019 | Poeze et al. |
| 2019/0374135 A1 | 12/2019 | Poeze et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2019/0386908 A1 | 12/2019 | Lamego et al. |
| 2019/0388039 A1 | 12/2019 | Al-Ali |
| 2020/0000338 A1 | 1/2020 | Lamego et al. |
| 2020/0000340 A1 | 1/2020 | Wojtczuk et al. |
| 2020/0000415 A1 | 1/2020 | Barker et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0192441 A1 | 6/2020 | Saravis |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256835 A1 | 8/2021 | Ranasinghe et al. |
| 2021/0275101 A1 | 9/2021 | Vo et al. |
| 2021/0290072 A1 | 9/2021 | Forrest |
| 2021/0290080 A1 | 9/2021 | Ahmed |

(56) References Cited

U.S. PATENT DOCUMENTS

| | | |
|---|---|---|
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |

OTHER PUBLICATIONS

U.S. Appl. No. 10/503,379, filed Dec. 10, 2019, Al-Ali et al.
U.S. Appl. No. 10/505,311, filed Dec. 10, 2019, Al-Ali et al.
U.S. Appl. No. 10/512,436, filed Dec. 24, 2019, Muhsin et al.
Edworthy, J., Reid, S. et al., (2017). Recognizability and localizability of auditory alarms, Cognition Institutre, in 58 pages.
Ellis, Daniel P.W., (2001). Detecting Alarm Sounds, Department of Electrical Engineering, in 4 pages.
FFT versus Direct Convolution—Special Audio Signal Processing (2018). https://www.dsprelated.com/freebooks/sasp/FFT_versus_Direct_Convolution.html. in 12 pages.
O'Brien, D., (2007). Using Audible Alarms in Medical Equipment (IEC 60601-1-8). Mallory Sonalert Products, Inc. in 3 pages.
Philip, Elizabha, (2009). Evaluation of Medical Alarm Sounds (Master thesis). New Jersey Institute of Technology, 1-84.
Pietila, G. and Cerrato, G., (2012). Sound Quality Guidelines for Non-Automotive Products. Sound & Vibration, www.SandV.Com. 8-14.
Raboshchuk, G., Quintana, S.G. et al., (2017). Automatic detection of alarm sounds in a noisy hospital environment using model and non-model based approaches, TALP Research Center, 1-19.
Szalai, J. and Mózes, F.E., (2016). Intelligent Digital Signal Processing and Feature Extraction Methods. International Publishing Switzerland, Chapter 2, 59-92.

* cited by examiner

PATIENT MONITOR ALARM SPEAKER ANALYZER

RELATED APPLICATIONS

The present application is a continuation of U.S. patent application Ser. No. 17/387,513, filed Jul. 28, 2021, titled Patient Monitor Alarm Speaker Analyzer, now U.S. Pat. No. 11,812,229, which is a continuation of U.S. patent application Ser. No. 16/920,604, filed Jul. 3, 2020, titled Patient Monitor Alarm Speaker Analyzer, now U.S. Pat. No. 11,082,786, which is a continuation of U.S. patent application Ser. No. 16/505,142, filed Jul. 8, 2019, titled Patient Monitor Alarm Speaker Analyzer, now U.S. Pat. No. 10,779,098, which claims priority to U.S. Provisional Patent Application Ser. No. 62/696,208, filed Jul. 10, 2018, titled Patient Monitor Alarm Speaker Analyzer, and U.S. Provisional Patent Application Ser. No. 62/745,096, filed Oct. 12, 2018, titled Patient Monitor Alarm Speaker Analyzer. All of the foregoing applications are hereby incorporated by reference in their entirety. Any and all applications for which a foreign or domestic priority claim is identified in the Application Data Sheet as filed with the present application are hereby incorporated by reference and made a part of the present disclosure.

BACKGROUND

Hospitals, nursing homes, and other patient care facilities typically include patient monitors at one or more bedsides in the facility. Patient monitors generally include sensors, processing equipment, and displays for obtaining and analyzing a medical patient's physiological parameters. Physiological parameters include, for example, respiratory rate, SpO2 level, pulse, and blood pressure, among others. Clinicians, including doctors, nurses, physician's assistants, and other medical personnel use the physiological parameters obtained from the medical patient to diagnose illnesses and to prescribe treatments. Clinicians also use the physiological parameters to monitor a patient during various clinical situations to determine whether to increase the level of medical care given to the patient.

Patient monitors capable of measuring pulse oximetry parameters, such as SpO2 and pulse rate in addition to advanced parameters, such as HbCO, HbMet and total hemoglobin (Hbt, THb, or SpHb) and corresponding multiple wavelength optical sensors are described in at least U.S. patent application Ser. No. 11/367,013, filed Mar. 1, 2006 and entitled Multiple Wavelength Sensor Emitters and U.S. patent application Ser. No. 11/366,208, filed Mar. 1, 2006 and entitled Noninvasive Multi-Parameter Patient Monitor, both assigned to Masimo Laboratories, Irvine, CA (Masimo Labs) and both incorporated by reference herein. Further, noninvasive blood parameter monitors and corresponding multiple wavelength optical sensors, such as Rainbow™ adhesive and reusable sensors and RAD-57™ and Radical-7™ monitors for measuring SpO2, pulse rate, perfusion index, signal quality, HbCO, and HbMet among other parameters are also available from Masimo Corporation, Irvine, CA (Masimo).

Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt or SpHb), as a few examples. Advanced physiological monitors and corresponding multiple wavelength optical sensors capable of measuring parameters in addition to SpO2, such as HbCO, HbMet and Hbt are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, which are each hereby incorporated by reference herein in their entirety. Further, noninvasive blood parameter monitors and corresponding multiple wavelength optical sensors, such as Rainbow™ adhesive and reusable sensors and RAD-57™ and Radical-7™ monitors for measuring SpO2, pulse rate, perfusion index (PI), signal quality (SiQ), pulse variability index (PVI), HbCO and HbMet among other parameters are also available from Masimo.

SUMMARY

An example patient monitor can diagnose whether its speaker is blocked or otherwise malfunctioning. For example, the monitor can include a processor that can diagnose the speaker by recording a microphone input signal. The processor can compare the microphone input signal to an expected alarm signal that should be output by the speaker. If the two do not match or reasonably correspond to one another, then the processor may increase the volume of the alarm to determine whether doing so can overcome an obstruction, noise, or potential malfunction. The microphone can again detect the speaker output and the processor can again make another comparison or analysis of the input with the speaker output. If the speaker output as detected via the microphone is still insufficiently loud, then the patient monitor may output an indication that the speaker has a problem.

For purposes of summarizing the disclosure, certain aspects, advantages and novel features of several embodiments have been described herein. It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers are re-used to indicate correspondence between referenced elements. The drawings are provided to illustrate embodiments of the inventions described herein and not to limit the scope thereof.

DETAILED DESCRIPTION

I. Introduction

Figure 1:
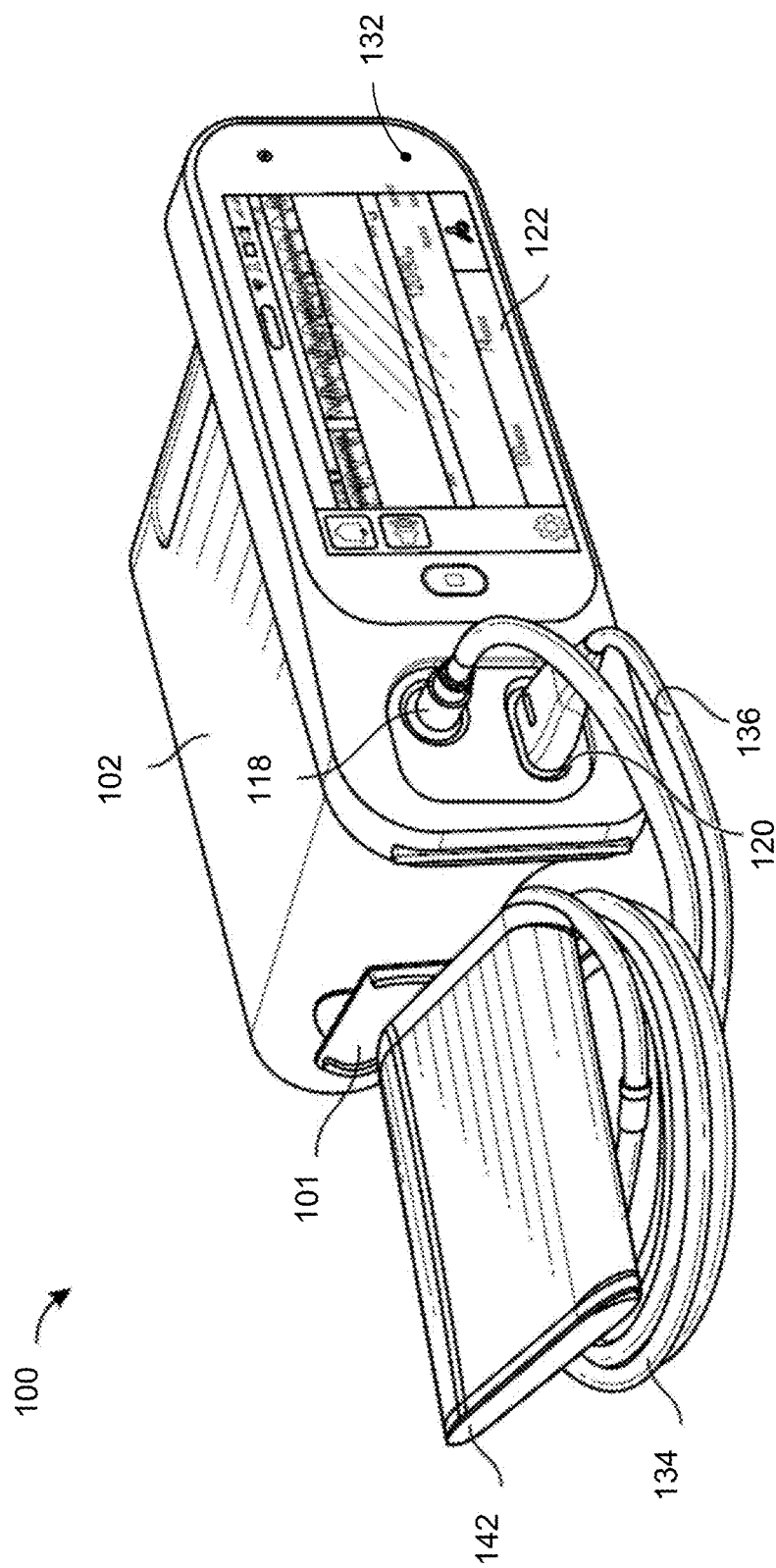
FIG. 1 depicts an example front perspective view of a patient monitoring system including a patient monitor and example sensor(s).

Alarm reliability is a critical requirement for patient monitors employed in healthcare. An alarm failure may result in patient injury or death. A robust alarm system can provide at least one of redundant alarms, drive circuit integrity checks, or alarm integrity checks to increase alarm reliability. An example approach for addressing alarm reliability is described in U.S. Pat. No. 7,962,188, filed Oct. 12, 2006, titled "Robust Alarm System" ("the '188 patent"), the disclosure of which is hereby incorporated by reference in its entirety.

Many modern patient monitors are portable and may be used in vehicles, such as ambulances and medical helicopters. However, when used in a vehicle, the patient monitor may be inserted into a portion of the vehicle such that the monitor's speaker is blocked, muffling or muting any alarms. Or, the speaker may not be blocked, but the volume may be turned down such that alarm sounds cannot be heard above the noise of the vehicle. Further, the acoustic environment of the vehicle (or any location the monitor is installed) may reflect the alarm sounds in such a manner that destructive interference acts as an unintentional echo cancellation-reducing the alarm volume. Similar problems may occur in a hospital or other clinical setting, for instance, where the monitor is placed in a stack of monitors that may block the monitor's speaker, or where other hospital sounds drown out the alarm sound. Likewise, a wearable patient monitor (for example, on an armband) may become blocked by linens or pillows on the patient's bed, muffling alarms. Any speaker may also malfunction, causing a reduction in its volume output.

To attempt to address these problems, the monitor can diagnose whether its speaker is blocked or otherwise malfunctioning (or at a too-low volume) and can output a visual and/or audible indication of this error. For example, the monitor can include a processor that can diagnose the speaker by recording a microphone input signal. The processor can compare the microphone input signal to an expected alarm signal that should be output by the speaker and/or to the actual alarm signal sent to the speaker. If the two do not match or reasonably correspond to one another, then the processor may increase the volume of the alarm to determine whether doing so can overcome an obstruction, noise, or potential malfunction. The microphone can again detect the speaker output, and the processor can again perform another analysis of the speaker output. If the speaker output as detected via the microphone is still insufficiently loud, then the processor may cause the display of the monitor to output an error or an indication that the speaker has a problem. The processor can also transmit the error over a network to a remote server for distribution to other clinician or technician devices. Further, the processor can cause a second speaker, such as a piezoelectric buzzer, to output an audible alarm.

II. Example Patient Monitors

FIGS. 1 through 4 depict an example patient monitoring system 100, including an example bedside/portable patient monitor 102, which can implement the speaker obstruction detection algorithms described herein. FIG. 4B depicts another example patient monitoring system 400, including an example wearable monitor 450, which can also implement the speaker obstruction detection algorithms described herein.

Referring specifically to FIG. 1, the example patient monitoring system 100 includes an example bedside/portable patient monitor 102 and example sensor(s) 142. The patient monitor 102, sometimes referred to as a point-of-care device, includes one or more ports 118, 120 for communicating with one or more sensors through sensor cables 134, 136, respectively. When the sensor(s) are coupled with a patient, the patient monitor 102 can analyze signals obtained from the sensor(s) to measure one or more of the patient's physiological parameters. The patient monitor 102 includes a display 122 for displaying the measured parameters. The patient monitor 102 can also include one or more speakers, buzzers, or the like (see, for example, FIGS. 2-4) that outputs audible alarms when a patient's physiological parameters reach dangerous levels or when other errors occur, such as a sensor falling off the patient.

Algorithms for detecting obstructed or malfunctioning speakers (also called loudspeakers), using an input detected by a microphone 132 (shown in one example location of many possible locations on the patient monitor 102), are described in detail below with respect to FIGS. 5-8. Example block diagrams of the patient monitor's 102 internal systems that can detect an obstructed or malfunctioning speaker are described below with respect to FIGS. 9-12.

The port 118 can enable communicating with a blood pressure sensor 142, such as a non-invasive blood pressure (NIBP) cuff. The port 120 can couple with a sensor (not shown) that can measure at least one of the following physiological parameters: oxygen saturation (SpO2), pulse rate (PR), perfusion index (PI), total hemoglobin (SpHb®), methemoglobin (SpMet®), carboxyhemoglobin (SpCO®), oxygen content (SpOC®), oxygen reserve index (ORi®), pleth variability index (PVi®), acoustic respiration rate (RRa®), respiration rate from pleth (RRp™), fractional arterial oxygen (SpfO$_2$™), rainbow Pleth Variability Index (RPVi™), or signal quality. In addition or alternatively, the patient monitor 102 can include a port for communicating with a capnography sensor (for example, a $CO_2$ sensor) so as to measure or determine parameters such as end-tidal carbon dioxide (etCO2), SpO2, Predictive or Temporal Artery Temperature, Masimo Rainbow® parameters (for example, RRa™, SpCO®, PVi®), electrocardiogram (ECG) (3-lead or other number of leads), combinations of the same, and the like. The patient monitor 102 can include a port (in addition to or alternative to those shown) for communicating with a biopotential sensor, a respiratory rate sensor, or a glucose sensor. In some cases, the patient monitor 102 can wirelessly communicate with sensor modules such as a blood pressure module, a pulse oximetry module, or a capnography module. Either port 118, 120 can be optional and may be omitted.

The patient monitor 102 can also serve as a connectivity hub for multiple third-party or proprietary devices (collectively referred to as remote modules 114). For example, the patient monitor can wired or wirelessly, for instance via Bluetooth, aggregate data from each of a plurality of remote modules 114. The patient monitor 102 can communicate with or integrate data from one or more devices such as a weight scale, glucometer, spirometer, stethoscope, a capnograph (such as the EMMA™ Capnograph marketed and sold by Masimo Corporation of Irvine CA ("Masimo")), a thermometer (such as the Caregiver marketed and sold by Masimo), a hemoglobin sensor (such as the Rainbow® DCI®-mini marketed and sold by Masimo), or a pulse oximeter (such as the MightySat™ Rx marketed and sold by Masimo), combinations of the same, or the like. If implemented as a monitoring hub, the patient monitor 102 can include any of the features described in U.S. Pat. No. 9,943,269, filed Oct. 10, 2014, titled "System for Displaying Medical Monitoring Data", the disclosure of which is hereby incorporated by reference in its entirety. Further, the patient monitor 102 may be battery powered or externally powered.

The display 122 of the patient monitor 102 can include touch screen capabilities. For example, a user can adjust a range of a displayed trend time by using intuitive finger gesture (for example, dragging, pinching, or spreading fingers). Further, the display 122 can be customizable such that a user can choose which information to display on the display 122. For example, the user can choose to display one or more of various waveforms, trends, values, timelines, or other data related to a patient's physiological parameters. The user can also customize the display using touchscreen input or optionally by menu-driven commands.

In some cases, the display 122 can display in portrait mode or landscape mode and can transition between display modes, for example, based on the orientation of the monitor 102. For example, the patient monitor can determine its orientation using a gyroscope or an accelerometer. Based on its determined orientation, the patient monitor 102 can display in landscape or portrait mode. In some cases, the display 122 can display in portrait mode when oriented vertically and can display in landscape mode when oriented horizontally. In some cases, a user can select landscape or portrait mode, which can cause the display 122 to lock the display 122 in the selected mode despite the orientation of the patient monitor 102.

In operation, the patient monitor 102 can receive a sensor signal associated with a sensor. Depending on the sensor, the patient monitor 102 can provide one or more drive signals to the sensor. The patient monitor 102 can receive (through wired or wireless connection) the sensor signal and can determines a conditioned signal. The conditioned signal may be transmitted or further processed by a signal processor, such as by buffering, digital filtering, smoothing, averaging, adaptive filtering, frequency transforms, or the like. The signal processor can derive a physiological parameter value responsive to the sensor signal. The resulting physiological parameter value may be a measurement calculated or derived from the conditioned signal, such as any of the physiological parameter values referred to above.

Figure 2:
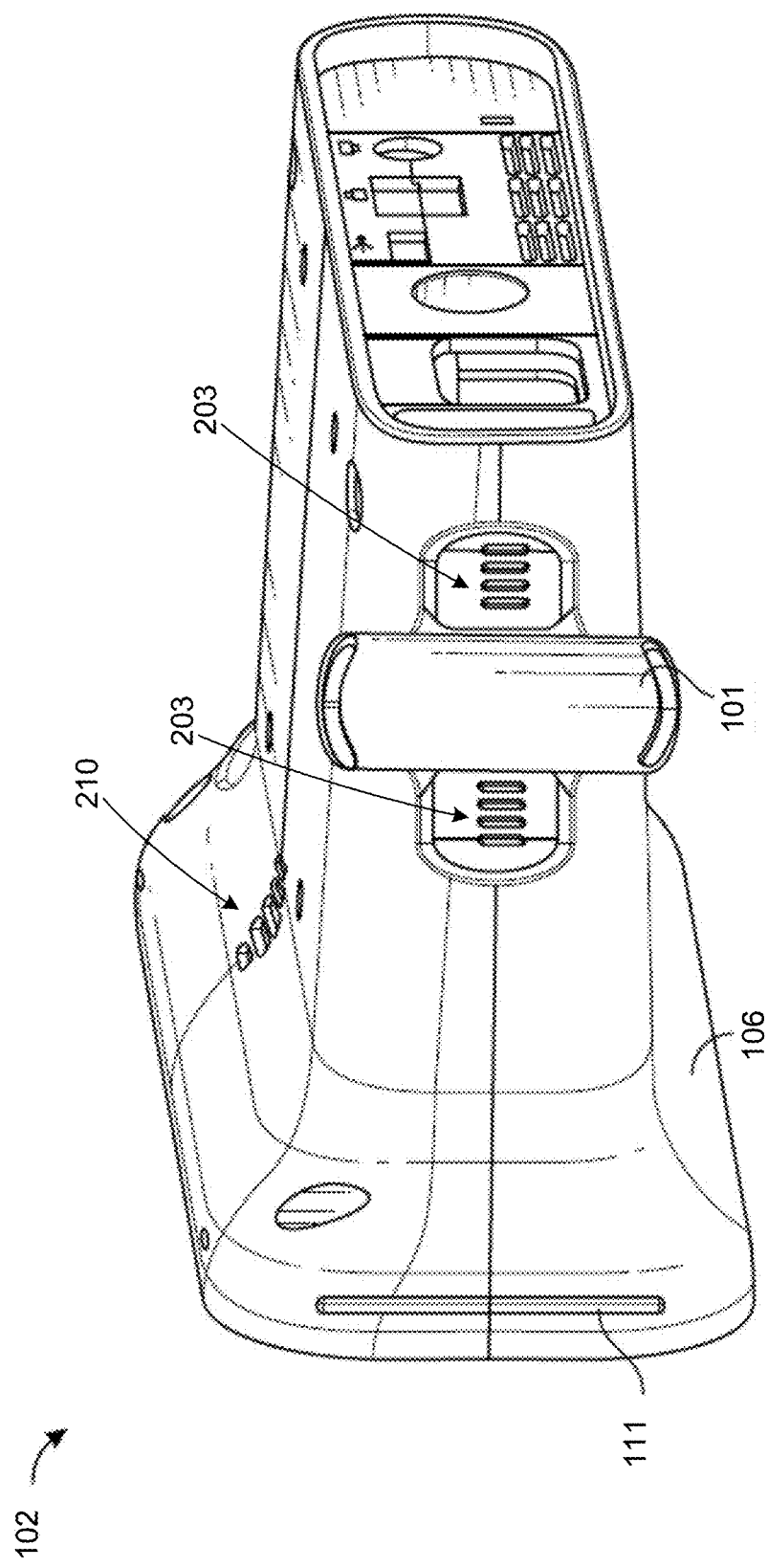
FIG. 2 depicts an example side perspective view of the patient monitor of FIG. 1.

FIG. 2 depicts an example side perspective view of the patient monitor 102 of FIG. 1. Among other features, the patient monitor 102 can include a vent cover 101 and a speaker grill 210. The vent cover 101 is shown in an open position in FIG. 2 and in a closed position in FIG. 1. The vent cover 101 can cover one or more ventilation holes 203 without occluding the ventilation hole(s) and also can provide a stabilization feature to the patient monitor 102. The vent cover 101 can swivel (for example, when rotated by a user) between various configurations (such as the closed and open positions shown in FIGS. 1 and 2, respectively). For instance, in a storage configuration, the vent cover 101 can fit within indentions of housing of the patient monitor 102 such that an outer surface of the vent cover 101 is at least partially flush with an outer surface of the housing. In a stabilizing configuration, the vent cover 101 (and a protrusion 111) can provide support to the patient monitor 102 when oriented in an upright position.

The speaker grill 210 is disposed on the top side of the patient monitor 102 in the depicted example. The speaker grill 210 can act as a protective cover and opening through which a speaker beneath the grill 210 may emit alarm sounds and other sounds. An example of such a speaker is described below with respect to FIG. 4. Placing the speaker grill 210 on the upper surface of the monitor 102 as shown can permit the front of the patient monitor 102 to be smaller in size and have cleaner lines. The placement of the speaker grill 210 can also permit the display of the patient monitor 102 to be larger with a smaller monitor form factor, which can increase the portability of the patient monitor 102.

Having a larger display in a smaller device can be beneficial for telemedicine applications where the display can show video of the patient or of a doctor. Also having a larger display in a smaller form factor can provide more information about different physiological parameters, including more parameter values, trends, and/or waveforms.

However, in this and other scenarios, as described above, a speaker may become obstructed, drowned out by noise, or otherwise malfunction. For example, the patient monitor 102 may be inserted into a portion of a vehicle such that the speaker grill 210 is blocked, obstructing the sound of any alarm that is emitted by the speaker. A similar effect may occur in a hospital or other clinical setting, for instance, where the monitor 102 is in a stack of monitors and a monitor above it may block the speaker grill 210.

To attempt to address these problems, the monitor 102 can diagnose whether its speaker is blocked or otherwise malfunctioning and can output a visual indication of this error. For example, the monitor 102 can include a processor that can diagnose the speaker by recording a microphone input signal using, for example, the microphone 132 of FIG. 1. The processor can compare the microphone input signal to an expected alarm signal that should be output by the speaker. If the two do not match or reasonably correspond to one another, then the processor may increase the volume of the alarm to determine whether doing so can overcome an obstruction, noise, or potential malfunction. The microphone 132 can again detect the speaker output and the processor can again make another comparison or analysis of the input with the speaker output. If the speaker output as detected via the microphone is still insufficiently loud, then the processor may cause the display of the monitor 102 to output an error or an indication that the speaker has a problem. The processor can also transmit the error over a network to a remote server for distribution to other clinician devices.

Although the monitor 102 is used herein as an example of a patient monitor that can include speaker diagnosis features, the speaker diagnosis features described herein can be implemented with any other type of patient monitor. Some other monitors, for instance, may have a speaker located in a position other than is shown in FIG. 2, such as on the front or the side or the bottom of the monitor.

Figure 3:
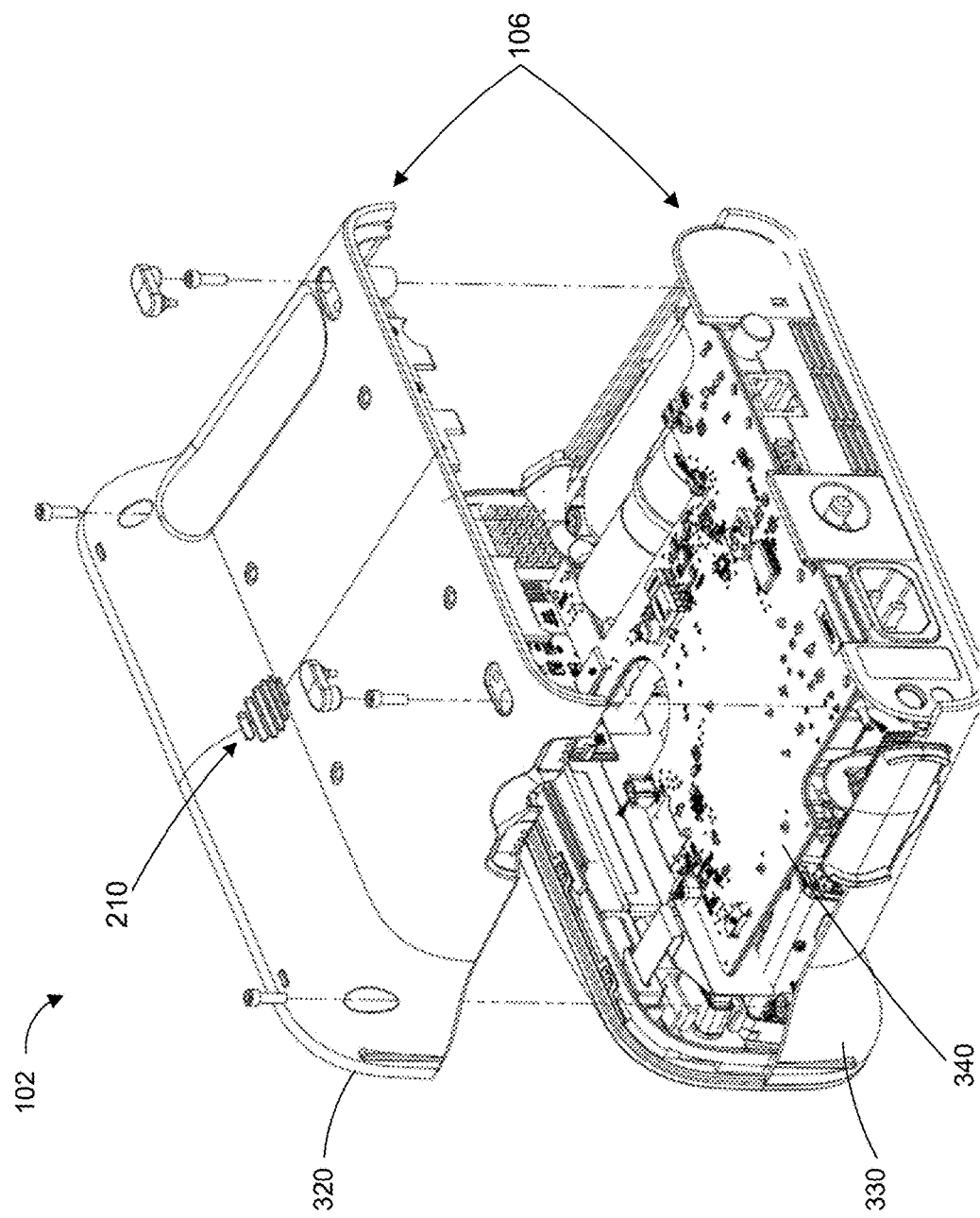
FIG. 3 depicts an example exploded perspective view of the patient monitor of FIG. 1.

Turning to FIG. 3, an example exploded view of the patient monitor 102 is shown. In this view, the housing 106 of the patient monitor 102 is shown separated into two distinct parts. In particular, the housing 106 is shown including a separate upper housing 340 and a lower housing 330.

The upper housing 320 includes the speaker grill 210 described above with respect to FIG. 2. The lower housing 330 includes a circuit board 340 that can include electronic components, such as a hardware processor that can process one or more algorithms for speaker diagnostics discussed herein.

Figure 4:
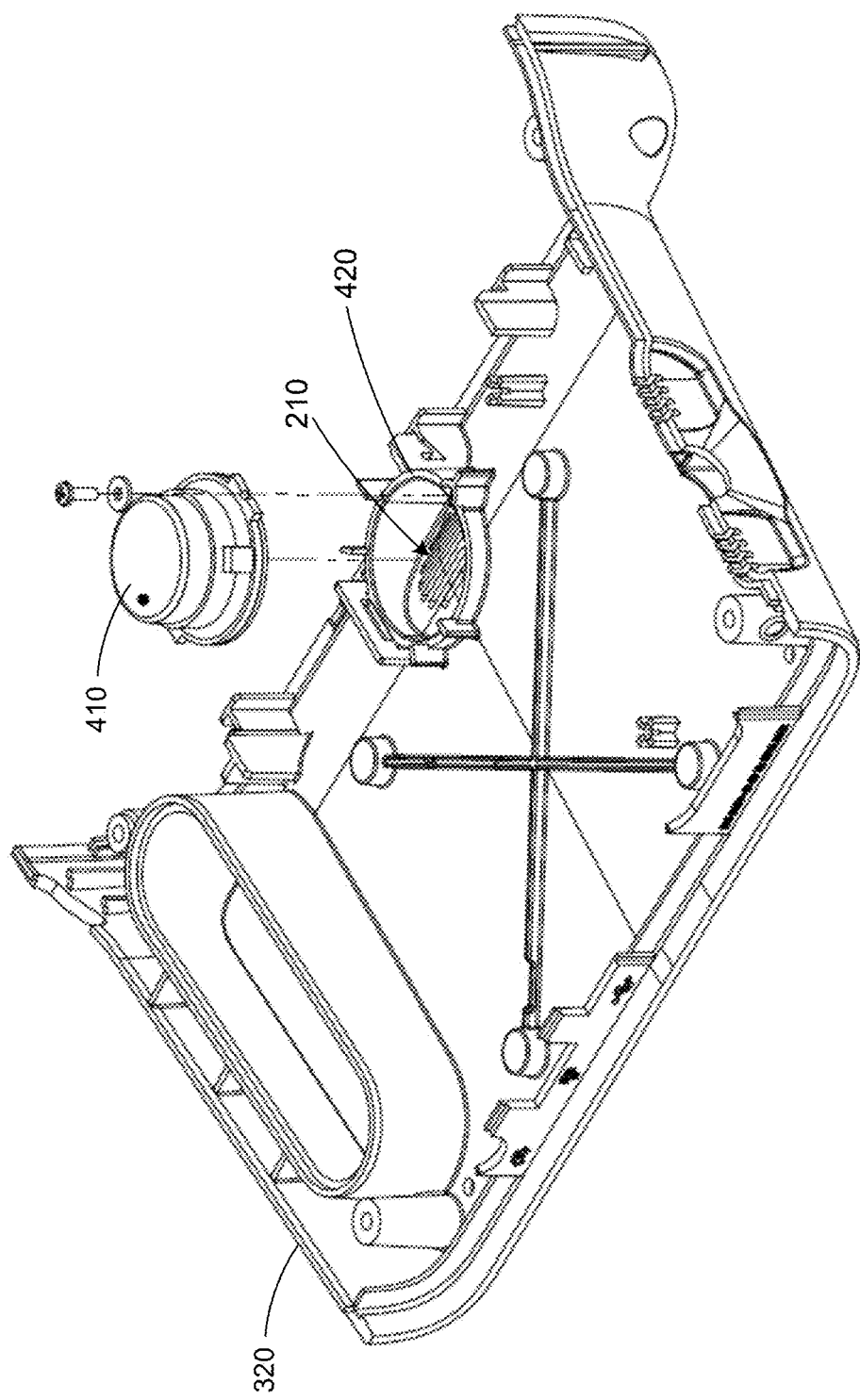
FIG. 4 depicts example internal speaker components of the patient monitor of FIG. 1.
Figure 4B:
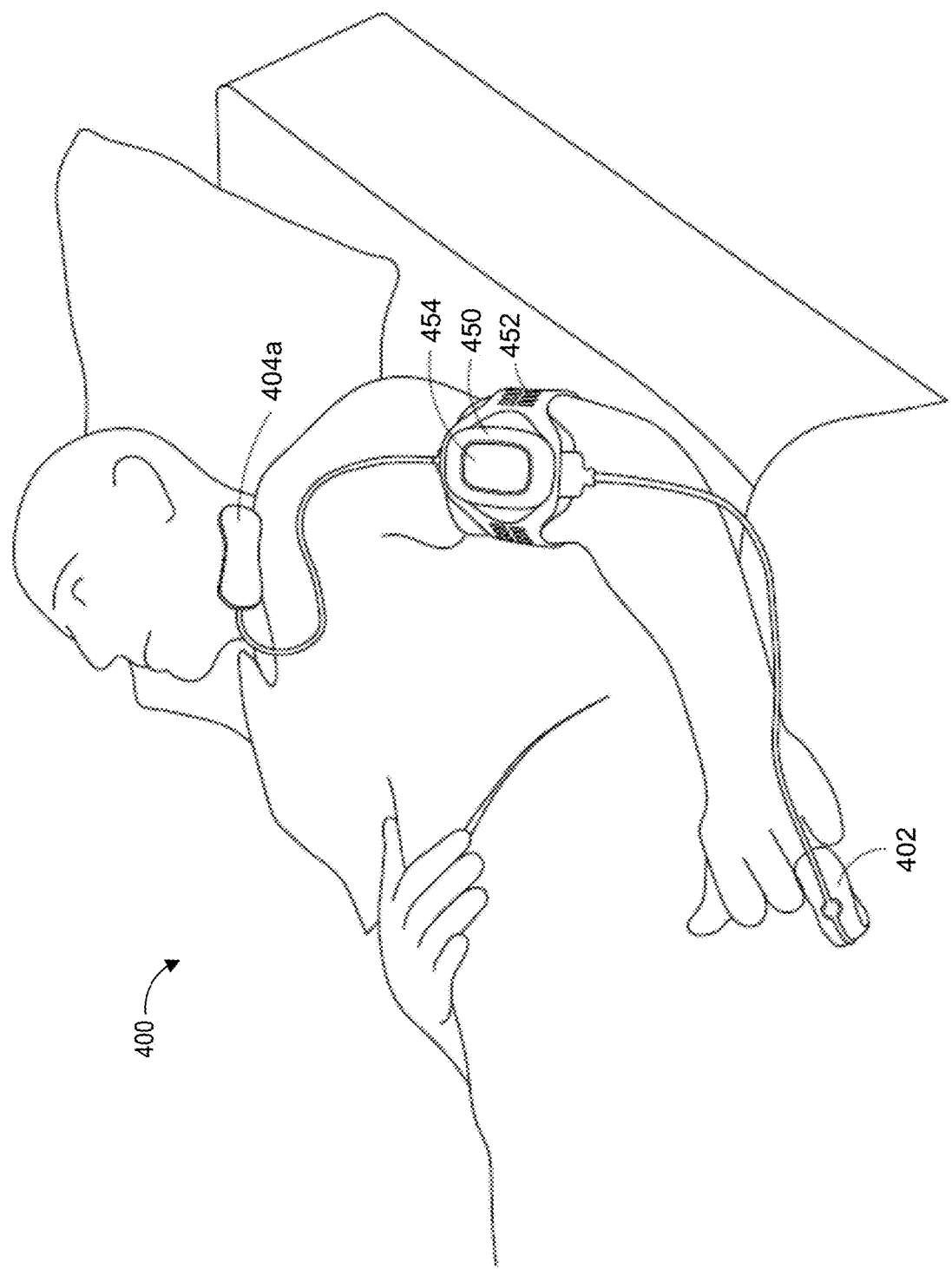
FIG. 4B depicts an example wearable patient monitor worn by a patient.

Turning to FIG. 4, the upper housing 320 of FIG. 3 is shown except that it is flipped over to reveal its underside, including the underside of the speaker grill 210. A speaker 410 is also shown in an exploded view apart from the upper housing 320. The speaker housing 410 can rest on a raised ridge 420 that encircles the speaker grill 210.

Although a single speaker is shown in FIG. 4, there may be multiple speakers in the patient monitor 102. For example, there may be two speakers, one of which is redundant to the other so that if one fails, the other continues to operate. Redundant speakers in this manner can continue to provide reliable alarms despite the failure of one speaker.

FIG. 4B depicts another example patient monitoring system 400, including an example wearable monitor 450, which can also implement the speaker obstruction detection algorithms described herein. The example wireless monitor 450 is shown secured to the arm of the patient. The wireless monitor 450 can be a fully functional stand-alone monitor capable of various physiological measurements. The wireless monitor can be small and light enough to comfortably be secured to and carried around on the arm of a patient. As shown, the example wireless monitor 450 connects to an acoustic respiration sensor 404A on a first side of patient monitor 450 and an oximeter sensor 402 on a second side of patient monitor 450. This configuration of connected sensors to opposite sides of the monitor can reduce cable clutter and entanglements. The wireless monitor 450 includes a screen 454 (which may be omitted in other implementations). The wireless monitor 450 can couple to and can be held to the arm of the patient by arm band 452, although other attachment mechanisms (such as a pocket or adhesive) are possible. The arm band 452 may, but need not, be an inflatable blood pressure cuff.

The wireless monitor 450 can be a standalone patient monitor, or it can wirelessly (or wired) transmit data to a bedside monitor using any of a variety of wireless technologies, such as Wi-Fi (802.11x), Bluetooth (802.15.2), cellular telephony, infrared, RFID, or the like.

Although not shown, the wireless monitor 450 can also have a speaker for outputting audible alarms.

III. Example Alarm Testing Algorithms

Figure 5:
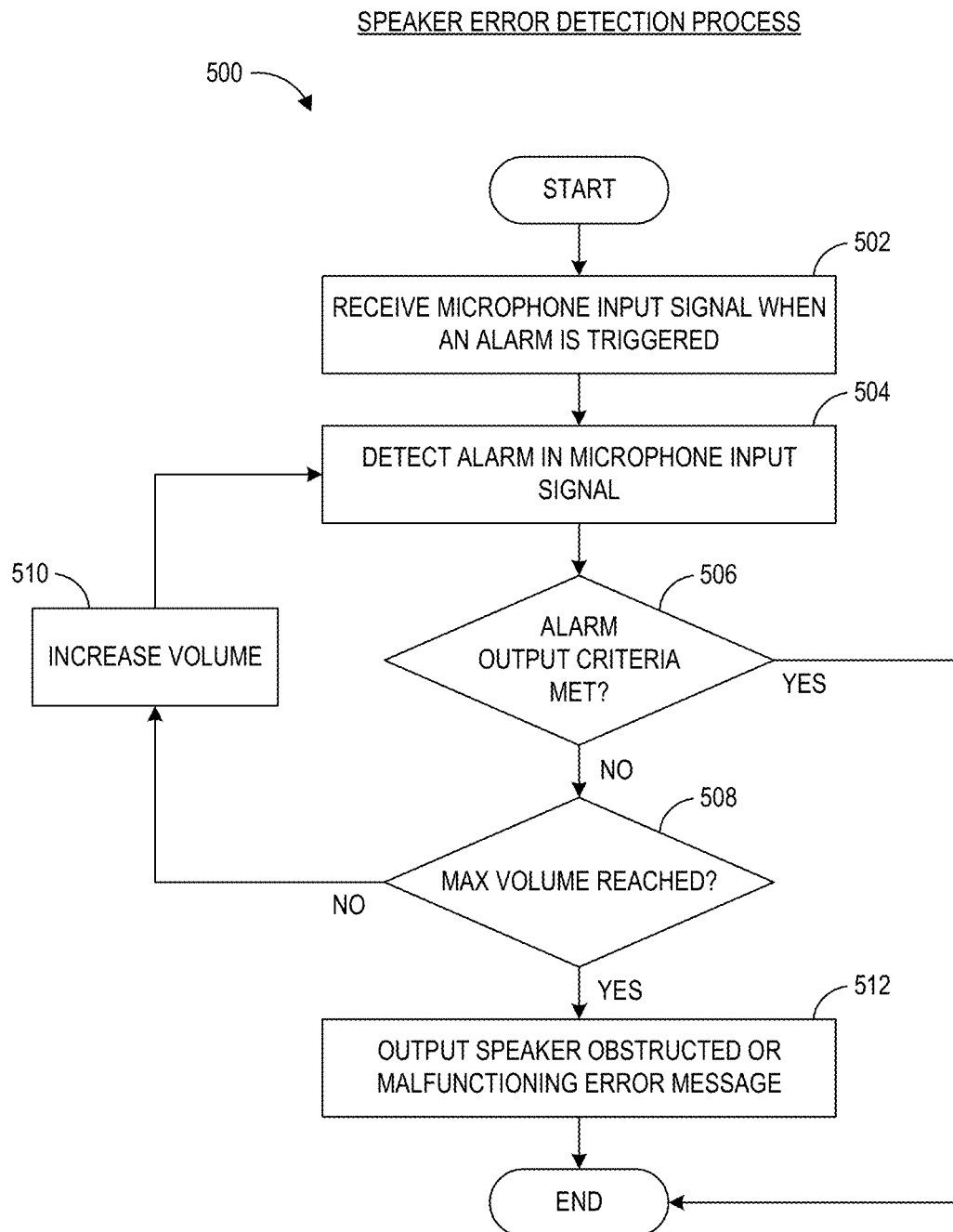
FIG. 5 depicts an example speaker error detection process.

Turning to FIG. 5, an example speaker error detection process 500 is shown, which is an example of the speaker diagnosis techniques described above. The speaker error detection process 500 can detect an error in a speaker, including an obstruction, partial obstruction, or malfunction of the speaker. The speaker error detection process 500 can be performed by a processor of the patient monitor 102 (or by the system of FIGS. 9 through 12, described below, which depict example schematic components of a patient monitor).

At block 502, the processor receives a microphone input signal when an alarm is triggered. The alarm may have been triggered by the processor detecting that a patient's physiological parameter (or parameters) have exceeded safe limits (such as low SpO2). The microphone input signal may be received from the microphone 132. The microphone input signal may be recorded in memory (for example, in a buffer) prior to further processing, or the signal may be processed in real time, as it is received.

At block 504, the processor detects (or attempts to detect) an alarm in the microphone input signal. This detection can include using one or more signal processing techniques to extract an alarm signal from the microphone input signal. Of course, it is possible that the processor may not be able to extract an alarm from the microphone input signal if the speaker is fully obstructed or malfunctioning.

It may or may not be a straightforward operation to obtain or detect the alarm in the microphone input signal. This is because the patient monitor 102 may be located in a noisy environment. Some examples of noisy environments that the patient monitor may be located in include a hospital room, an ambulance, or a helicopter. Because of the noise that may be inherent in such environments, it may be difficult to distinguish whether the speaker is functioning properly or whether noise is drowning out or otherwise muddling the alarm signal.

Accordingly, the signal extraction technique employed at block 504 can include filtering. For example, filtering may be employed to look in expected bands of the microphone input signal for identifiable portions of the alarm signal. Filtering may be performed using low pass, band pass, notch, or high pass filters or some combination of the same, such as a filter bank. Another technique that may be used includes cross correlation of an output alarm signal sent to the speaker with the microphone input signal. Further, statistical approaches, noise reduction filtering, envelope detection, smoothing, comb filtering, or harmonic comb filtering may also be performed.

Many alarm signals may have a plurality of beeps in a pulse train which may be detectable in the time domain. Thus, the detection of the alarm input in the microphone input signal could also involve performing time domain analysis, such as searching for a pulse train of beeps.

At block 506, the processor compares the detected (purported) alarm signal with one or more alarm output criteria and determines whether the one or more alarm output criteria have been met. The alarm output criteria can include one or more rules, processes, or techniques for analyzing the detected alarm in the microphone input signal. In general, the closer that the detected alarm characteristics match one or more desired alarm characteristics, the more likely the detected alarm is a suitable alarm. If the detected alarm (or purported alarm) does not match the alarm criteria, it is possible that the speaker is blocked or otherwise malfunctioning.

The alarm output criteria may specify, for instance, that a detected (purported) alarm having a volume, loudness, or magnitude lower than a certain threshold may indicate a possible obstruction or speaker malfunction. The alarm output criteria can be evaluated using time domain and/or frequency domain techniques. Some example time domain techniques can include analyzing the magnitudes of pulses in a train of pulses to determine whether those magnitudes are greater than a threshold. Further, another example time domain technique can include analyzing the number of pulses in a pulse train to confirm the correct number of beeps is being reproduced. Example frequency domain techniques can include analyzing magnitudes of spectral peaks, performing cross-correlations, and so forth (see, for example, FIGS. 6-8B).

Further, time domain and frequency domain analysis can be performed together by obtaining a spectrogram of frequency spectra corresponding to the detected alarm signal over time. This spectrogram can be constructed with the short time Fourier transform (STFT) or another transform (additional examples of which are described with respect to FIG. 6 below).

With continued reference to FIG. 5, if the alarm output criteria has been met, then the process 500 ends because the speaker can be determined to be functioning correctly. However, if the alarm output criteria is not met, then at block 508 the processor can determine whether a maximum volume of the speaker has been reached. If not, then at block 510, the processor can increase the volume that is applied to the alarm signal. The alarm volume may be increased at block 510 in increments, or the alarm volume may be increased at block 510 to maximum volume immediately. A possible advantage of increasing the volume in increments may be avoiding startling a user who may not be expecting a large change in volume. Conversely, a possible advantage of increasing the volume to the maximum volume right away may be that the problem with the speaker (if there is one) may be detected more quickly. After increasing the alarm volume, the process 500 can loop back to block 504 and again detect an alarm in the microphone input signal and again evaluate whether the detected alarm meets one or more alarm output criteria (block 506).

Blocks 504 through 510 may thus continue in a loop until a maximum volume is reached. If the maximum volume is reached without the one or more alarm output criteria being met, then at block 512 the processor can output a speaker obstructed or malfunctioning error message on the display of the patient monitor. This message can also be output to a remote server, for example, as a notification or escalation.

Figure 6:
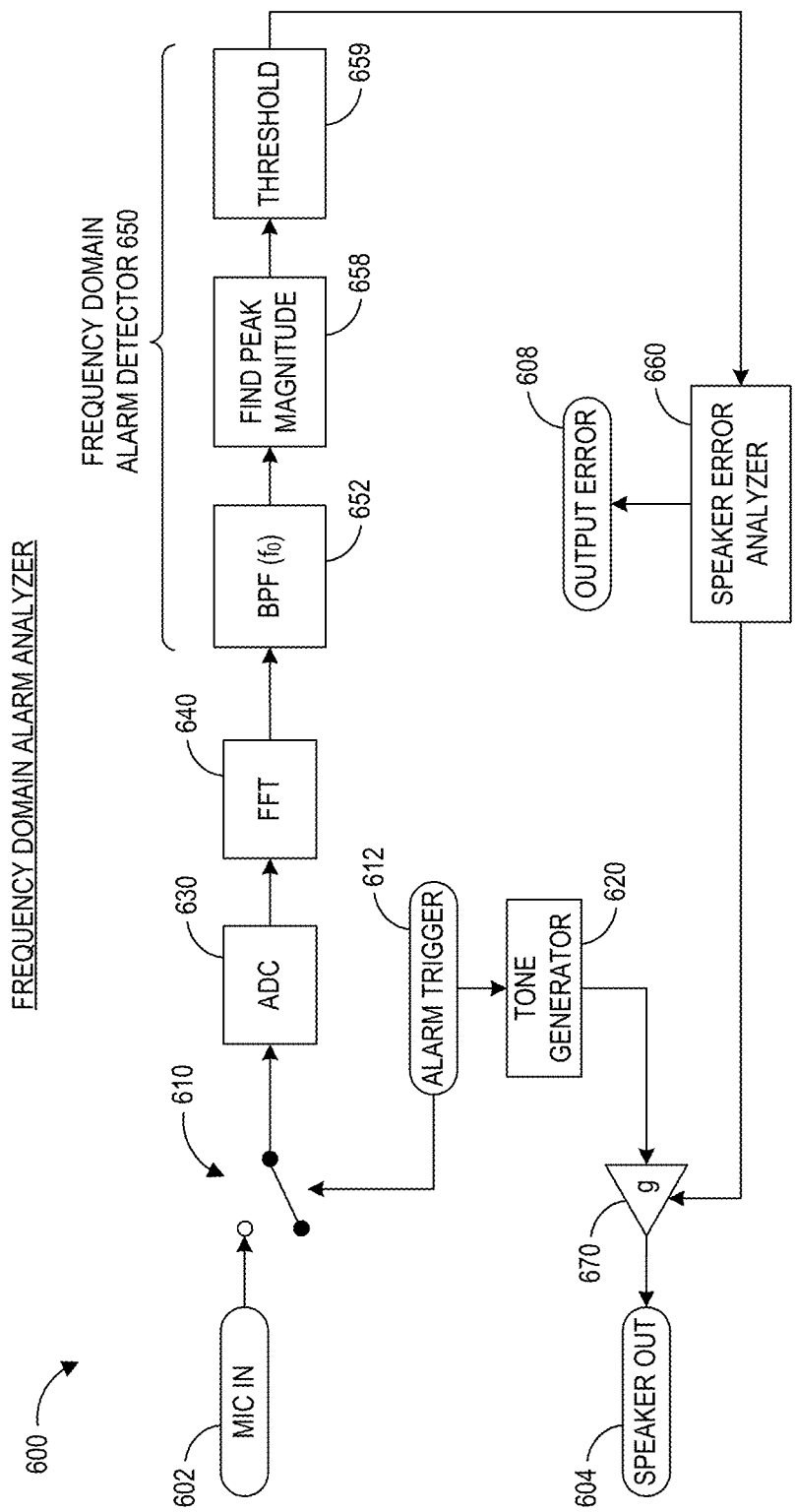
FIGS. 6 and 7 depict example frequency domain alarm analyzers.

Turning to FIG. 6, an example frequency domain alarm analyzer 600 is shown. The alarm analyzer 600 can be implemented by the processor described herein, or more generally, by any patient monitor. Many alarms may be just a single tone, such as a sine wave played at a specific frequency through a speaker. The frequency domain alarm analyzer 600 represents one example way to detect an alarm that includes a single tone. Other example analyzers for analyzing multiple alarm tones are described below with respect to FIGS. 7-8B.

The single tone alarm analyzer 600 can receive a microphone input 602. The microphone input can be received from the microphone 132 of FIG. 1. A switch 610 can determine whether the microphone input is received for processing or is not received. The switch 610 can be logical, implemented in software, or it can be an actual switch in hardware. For example, if the switch is logical, the ADC 630 can be placed before the switch 610.

The switch 610 may be actuated by an alarm trigger 612. The alarm trigger 612 can be triggered whenever the processor (or software running in the processor) determines that an alarm condition is present, such as low SpO2. When the alarm trigger 612 occurs, two things can happen either at the same time or substantially the same time, or one right after the other. The alarm trigger 612 can cause a tone generator 620 to output an alarm tone, which may be a waveform corresponding to the alarm sound. The output of the tone generator 620 can be provided to a gain block 670, which can apply a gain to the tone generated by the tone generator 620. The gain can be a volume setting (or can be proportional to a volume setting) of the alarm. The output of the gain block 670 can be an alarm signal that can be provided to a speaker as a speaker output 604.

The alarm trigger 612, in addition to triggering the generation of an alarm to be output to the speaker, can also generate a signal or logical code that causes the logical switch 610 to receive the microphone input signal 602. Thus, the microphone may be recording when the alarm is sounded but not at other times. An analog to digital converter (ADC) 630 can receive the microphone input signal and convert the analog microphone input signal to a digital input signal including, for example, by performing preamplification and sampling. The output of the ADC 630 may be a digital signal that can be supplied to an FFT (Fast Fourier Transform) block 640.

The FFT block 640 can perform a mathematical transform, the FFT, on the digital signal to convert the digital signal from a time domain representation to a frequency domain representation. Other types of transforms may be used instead of or in addition to the FFT, such as the short time Fourier transform (STFT) (which may be implemented by the FFT), a wavelet transform, or the Hilbert-Huang transform. However, the FFT block 640 can be optional, and instead of performing alarm tone detection in the frequency domain, alarm tone detection can be performed in the time domain (see, for example, FIG. 8). Alternatively, alarm tone detection may be performed in a combination of the time domain and the frequency domain (see, for example, FIG. 8B). For illustration purposes, the remainder of the specification focuses primarily on frequency domain techniques.

The output of the FFT block 640 can be a frequency domain representation of the microphone input signal, which is supplied to an alarm tone detector 650. There are many different ways to implement detection of an alarm signal, and thus the examples shown in FIG. 6 (and subsequent Figures) are non-limiting examples of ways to detect the alarm signal. The example alarm tone detector 650 shown includes a band pass filter 652, a peak magnitude finder 658, and a threshold detector 659.

The band pass filter 652 may have a center frequency $f_0$ that is at the expected location of the alarm tone in the frequency domain representation of the microphone input signal. The band pass filter 652 may optionally be tuned with a high Q-factor such that the band pass filter is very narrow in bandwidth, so as to focus on a small amount of frequency content around the center frequency of the band pass filter. Since a single tone alarm may have its energy concentrated at or around one frequency, a narrow bandpass filter can focus on that frequency and optionally a small amount of surrounding frequencies. The band pass filter 652 is optional and may be omitted.

The peak magnitude finder 658 can identify the magnitude of the peak. The threshold detector 659 can compare the peak with the threshold to determine whether the peak has a magnitude greater than a threshold.

The speaker error analyzer 660 can essentially perform blocks 506 through 510 of the process 500 after the alarm tone detector 650 has performed block 504 of the process 500. For instance, the speaker error analyzer 660 can determine whether one or more alarm output criteria are met as described above with respect to FIG. 5, for example, by determining whether the peak exceeded the threshold and therefore likely corresponds to a sufficiently loud alarm. If not, the speaker error analyzer 660 can determine whether a maximum volume has been reached, and if not, can increase the volume by outputting an instruction to the gain block 670 to increase the gain. The tone generator 620 input to the gain block 670—the alarm waveform—can then be amplified further to attempt to detect an alarm sound with the alarm tone detector 650.

If the speaker error analyzer 660 determines that the maximum volume has been reached without the alarm output criteria being met, then the speaker error analyzer 660 can provide an error output 608. The error may indicate that the speaker has been obstructed, or it may be malfunctioning or have some other error. The error output 608 can be textual in nature or it can be a graphical display or icon, such as an icon depicting a speaker with a line through it in red (potentially flashing) or the like. The error output 608 may also be a remote notification that the speaker error analyzer 660 causes to be provided to a remote server so that clinicians can access the information about the error remotely, and so that if a clinician does not respond based on the error then the remote server can cause the error to be escalated as a new alarm to other clinicians or to a technician who can repair the speaker. Further, the error output 608 may be an audible sound transmitted through a backup speaker installed in the patient monitor, which may be a piezoelectric buzzer or the like.

As described above, there may be a variety of alarm output criteria that the speaker error analyzer 660 uses either in the time domain or the frequency domain. In this example, the peak magnitude is supplied to the speaker error analyzer 660 by the peak magnitude finder 658. The speaker error analyzer 660 can analyze the threshold output from the threshold block 659. If the peak magnitude meets or exceeds the threshold, the speaker error analyzer 660 can indicate that the speaker is functioning properly and not increase the gain at the gain block 670. Conversely, if the peak magnitude is below the threshold, the speaker error analyzer 660 can output that the speaker is not functioning properly (at block 608) and increase the gain at the gain block 670.

In some instances, the speaker error analyzer 660 can output a more granular indication of a problem (at block 608). For instance, the speaker error analyzer 660 may be able to indicate that the speaker is partially blocked rather than completely blocked. The speaker error analyzer 660 may determine partial blockage by determining that the peak magnitude received from the peak magnitude finder 658 is between two thresholds but not so low as to indicate blockage. Other variations are possible.

Figure 7:
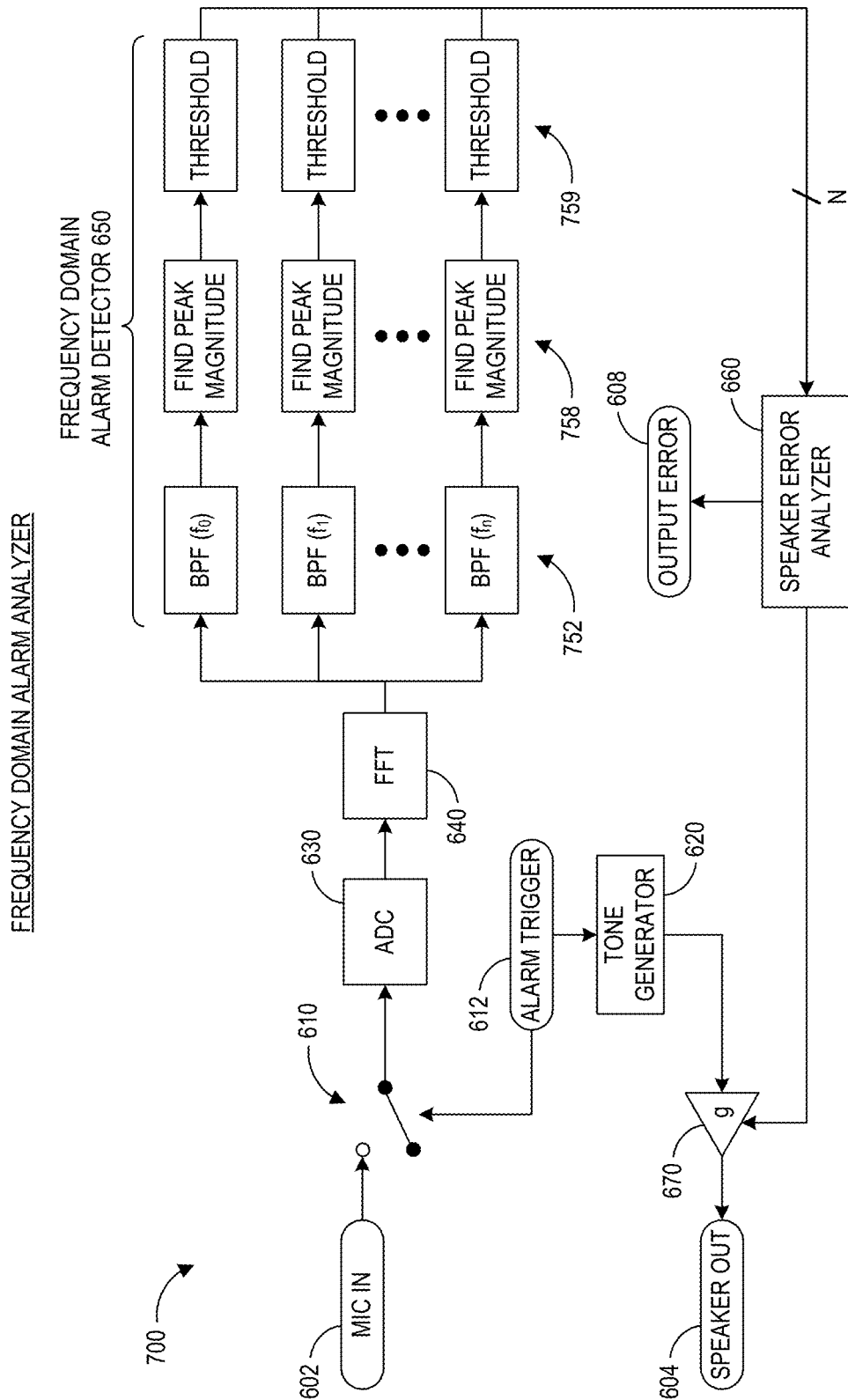

Turning to FIG. 7, another example frequency domain alarm analyzer 700 is shown. Many alarm signals have harmonics, including alarm signals that are formatted according to certain industry standards, an example of which is described below with respect to FIG. 13. The frequency domain alarm analyzer 700 incorporates much of the functionality of the frequency domain alarm analyzer 600 of FIG. 6 and adds additional functionality to detect multiple harmonic tones.

For instance, a microphone input 602 can be received. A switch 610 can selectively supply the microphone input signal 602 to an ADC 630, which can supply a digital signal to an FFT 640. (Alternatively, the ADC 630 can be placed before the switch 610, and the switch 610 may be logical—implemented in software.) The FFT 640 can output a spectrum to an alarm detector 750, which can include features of the alarm detector 650 but in multiple signal paths. For instance, instead of a single band pass filter, a band pass filter bank 752 can be used. The band pass filter bank 752 can be find a fundamental frequency and harmonics of a harmonic alarm signal, or more generally, multiple expected peaks in the signal. Three signal paths are shown, but ellipses indicate that any number of signal paths may be used, including four or more.

The remaining blocks 754 through 758 can have the same or similar functionality as the corresponding blocks in FIG. 6 for the fundamental and each harmonic (note: the fundamental is also sometimes called the first harmonic). For example, the result of the alarm detector 750 can be that the peak magnitude can be found and thresholded for each fundamental and harmonic in the microphone input signal.

The speaker error analyzer 660 can analyze the outputs of the peak threshold blocks 759 and can perform similar criteria as in FIG. 6 but with multiple tones. For example, the speaker error analyzer 660 can determine whether each of the peaks is lower than a low threshold (indicating possible full obstruction) or between the low threshold and a higher threshold (indicating a possible partial obstruction). However, other criteria may be used with multiple peaks. For instance, the speaker error analyzer 660 can compare the relative magnitudes of the peaks. If the peaks are above a threshold, but their relative magnitudes differ too greatly, then the speaker nevertheless may be muffled or garbled due to an obstruction or partial obstruction. For instance, if a speaker is blocked then the higher frequency harmonics are more likely to be attenuated than lower frequency harmonics (including the fundamental frequency). Thus, identifying attenuated higher frequencies can suggest that the speaker is blocked or partially blocked.

If there is little or no evidence of spectral peaks, or if their magnitudes are very small, then the speaker may be malfunctioning. But it may be easier to determine a malfunctioning harmonic alarm versus a malfunctioning single tone alarm. A single tone alarm may be mimicked by noise, but when there are multiple harmonics, it can be more difficult to mimic all of the harmonics with noise. Thus, the speaker error analyzer 660 may be able to determine whether the speaker is malfunctioning versus obstructed by simply detecting whether there are actual harmonics of the fundamental frequency. Absent harmonics of the fundamental, it is more likely that the speaker is malfunctioning versus merely obstructed. Likewise, if the fundamental is not present but one or two harmonics are present, then that can also suggest that the speaker may be malfunctioning as opposed to being muffled. The speaker error analyzer 660 can output an appropriate error 608 accordingly, which may be the same as described above with respect to FIG. 6. Other components shown can have the same or similar functionality as described above with respect to FIG. 6.

Figure 8:
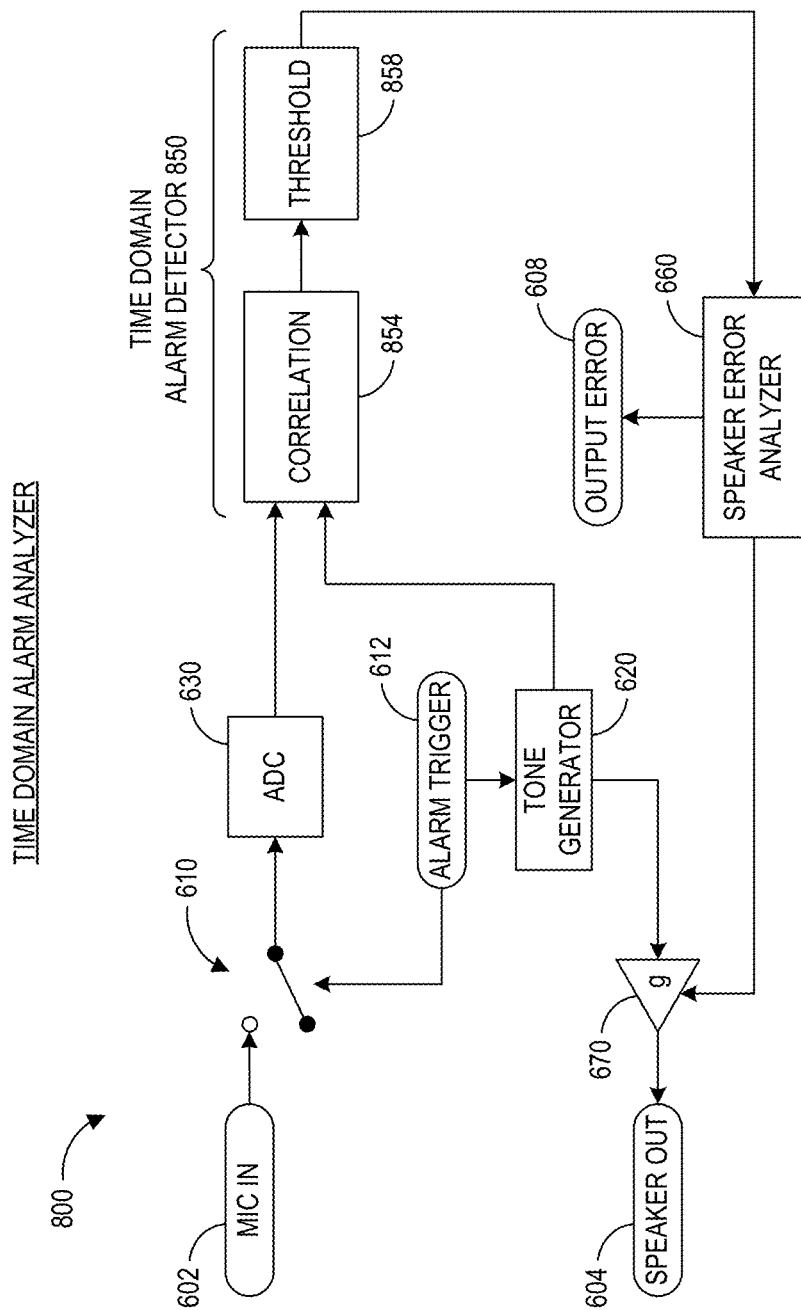
FIG. 8 depicts an example time domain alarm analyzer.

Turning to FIG. 8, another example alarm analyzer 800 is shown. The alarm analyzer 800 is an example time domain alarm analyzer. The time domain alarm analyzer 800 can be used to detect single or multiple tone alarms or more complex alarms that may have multiple characteristics including changing frequencies, changing magnitudes and so forth. The time domain alarm analyzer 800 differs in some respects from the previous alarm analyzers but can include similar components.

The output of the ADC 630 can be supplied to a correlation block 854. The correlation block 854 can perform a correlation comparison (such as a cross correlation or autocorrelation) of the microphone recorded signal with the output signal sent to the speaker from the tone generator 620. Doing so may create a correlation output signal that can be analyzed by a threshold detector 858. The threshold detector 858 can determine whether the correlation between the input signal's alarm and the output signal are sufficiently correlated. For example, the threshold detector 858 can determine whether a highest peak in the correlation output exceeds a threshold, or the threshold detector 858 can search for predetermined patterns in the correlation output. Many other pattern matching algorithms are possible besides threshold detection, including algorithms that detect patterns in a spectrogram, clustering algorithms, linear prediction, and the like.

If the detected alarm is sufficiently correlated with the output alarm, then the speaker error analyzer 660 may determine that there is no error. If not, the speaker error analyzer 660 may determine that there is an error and perform according to the processes and examples previously provided, adjusting the gain 670 and/or outputting the error 608.

Figure 8B:
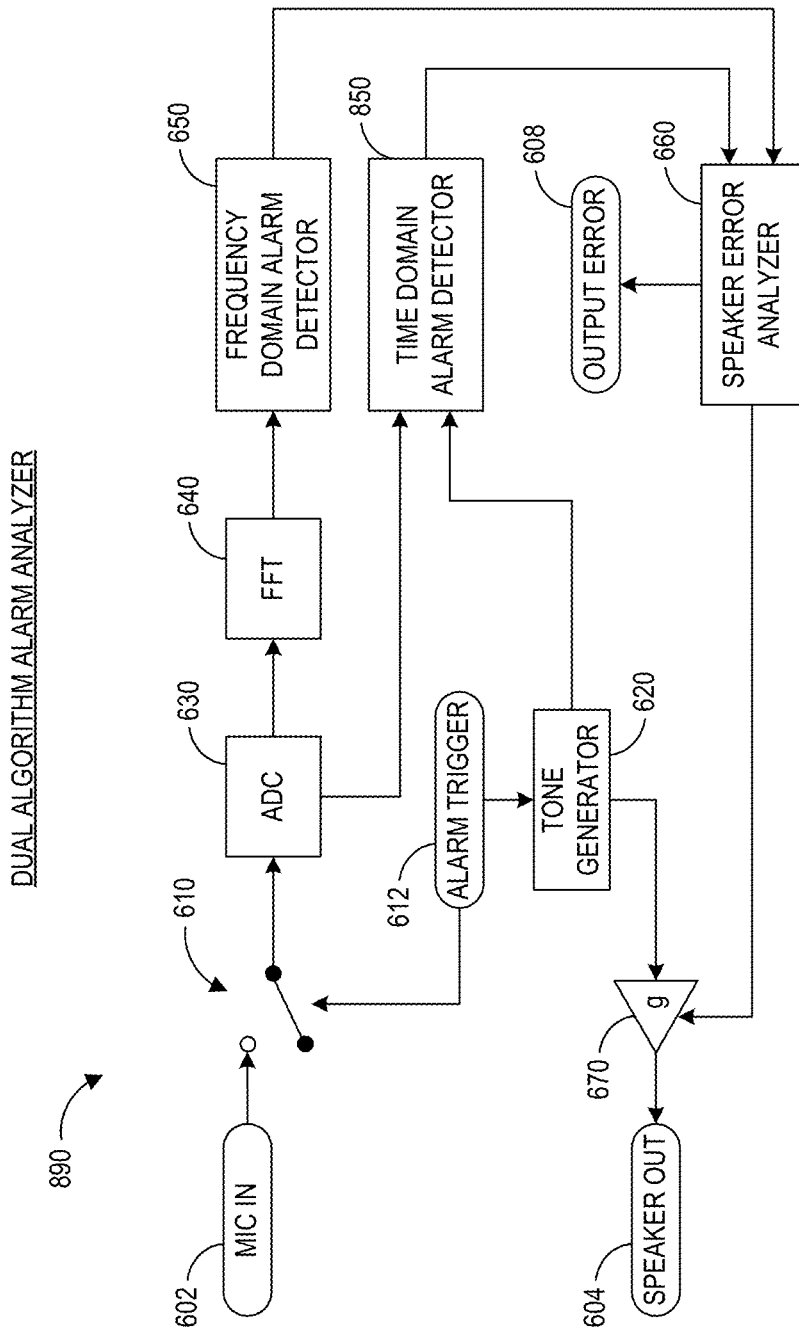
FIG. 8B depicts an example dual algorithm alarm analyzer.

FIG. 8B depicts an example dual algorithm alarm analyzer 890. The example dual alarm analyzer 890 includes both a frequency domain alarm detector 650 and a time domain alarm detector 850. These detectors 650, 850 can work as described above with respect to FIGS. 6-8. The output of these detectors can be provided to the speaker error analyzer 660. The speaker error analyzer 660 can use decision logic to determine whether to output an error 608 and/or adjust the gain 670 based on the output of both detectors 650, 850. For example, the decision logic may determine that if either detector output is below a threshold or otherwise indicates the alarm to be low volume, the speaker error analyzer 660 can determine that an error has occurred and perform the functions of the process 500, blocks 506 through 512. Or, the speaker error analyzer 660 can determine that an error has occurred only if both the detectors 650, 850 output errors (for example, output below-threshold outputs as described above).

IV. Example Patient Monitor Block Diagrams

Figure 9:
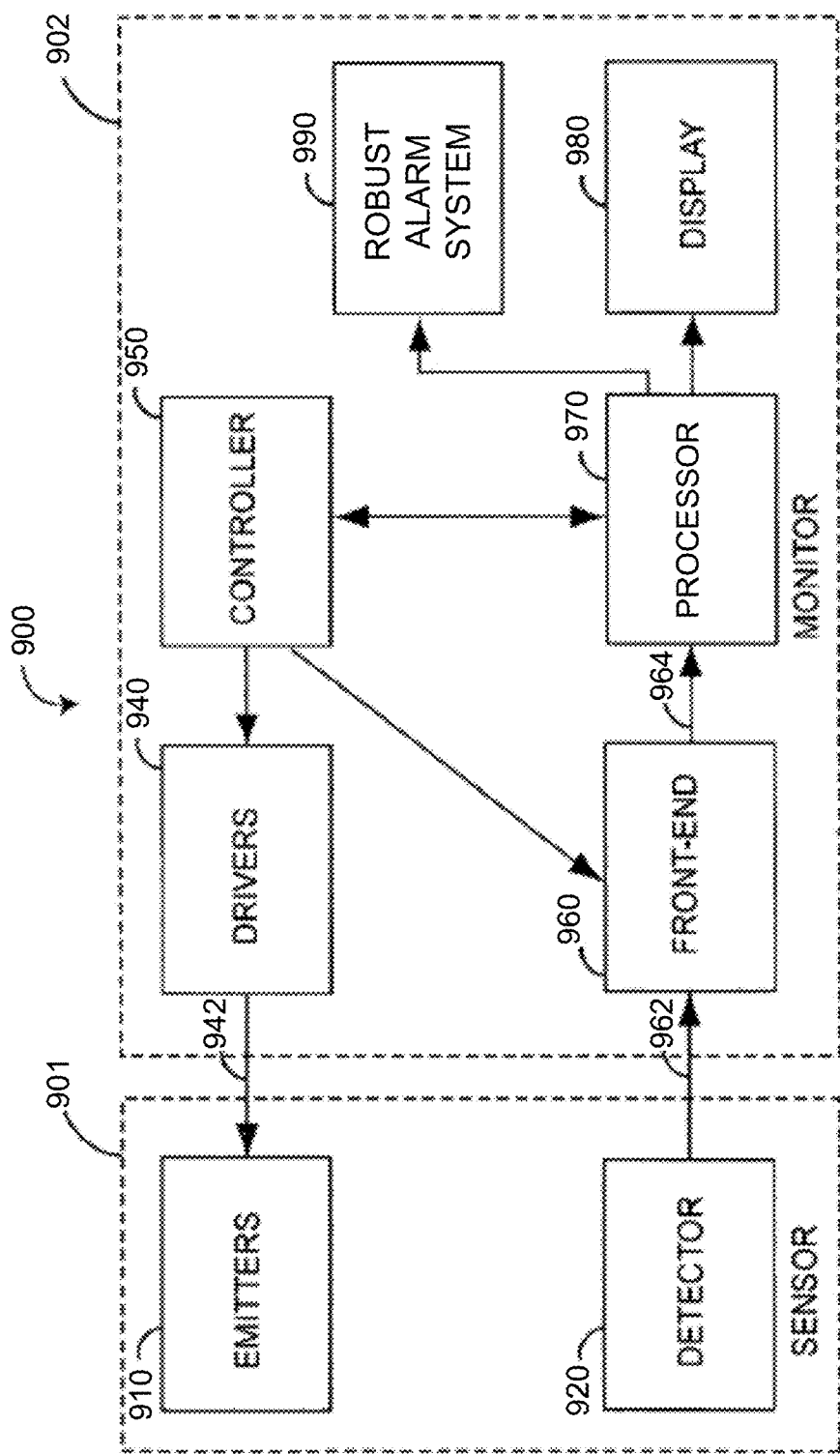
FIG. 9 depicts an example block diagram of a pulse oximetry system having a robust alarm system.

FIG. 9 illustrates an example block diagram of a pulse oximetry system 900 that can implement these alarm reliability features. The oximetry system 900 includes a patient monitor 902, which is a schematic example of the patient monitor 102 (but which can also be used in another type of patient monitor). The pulse oximetry system 900 can measure the oxygen saturation level of arterial blood, an indicator of oxygen supply, as well as any of the other physiological parameters discussed herein. The pulse oximetry system 900 also includes a sensor 901 that can provide a sensor signal 962 to a pulse oximeter 902. The sensor 901 has emitters 910 and a detector 920 and can be attached to a patient at a selected tissue site, such as a fingertip, foot, forehead, or earlobe. The emitters 910 can transmit light having red and IR wavelengths into the tissue site. The detector 920 can generate the sensor signal 962 in response to the intensity of the emitter-transmitted light after attenuation by pulsatile blood flow within the tissue site. An example pulse oximetry sensor, which can be used as the sensor 901, is described in U.S. Pat. No. 6,088,607, filed Jan. 28, 1997, entitled Low Noise Optical Probe, the disclosure of which is hereby incorporated by reference in its entirety.

The monitor 902 includes drivers 940, a controller 950, and a front-end 960. The drivers 940 can activate the emitters 910 according to the controller 950, and the front-end 960 can condition and digitize the resulting sensor signal 962. The monitor 902 also has a hardware processor 970, a display 980, and a robust alarm system 990. The processor 970 can be a central processing unit (CPU), a digital signal processor (DSP), or a graphics processing unit (GPU), which can input the conditioned and digitized sensor signal 964 and calculate oxygen saturation along with pulse rate or other physiological parameters described herein. (Additional examples of types of processors that may correspond to the processor 970 are described below.) The display 980 can provide a numerical readout of a patient's oxygen saturation and pulse rate, as well as trends or waveforms. The robust alarm system 990 can provide an audible indication when oxygen saturation or other physiological parameters are outside of preset limits, as well as self-monitor the health of the alarm system 990. An example pulse oximeter or patient monitor, which can be used as the patient monitor 902, is described in U.S. Pat. No. 8,942,777, filed May 25, 2007, entitled Signal Processing Apparatus, which is assigned to Masimo Corporation, Irvine, CA, the disclosure of which is hereby incorporated by reference in its entirety.

Figure 10:
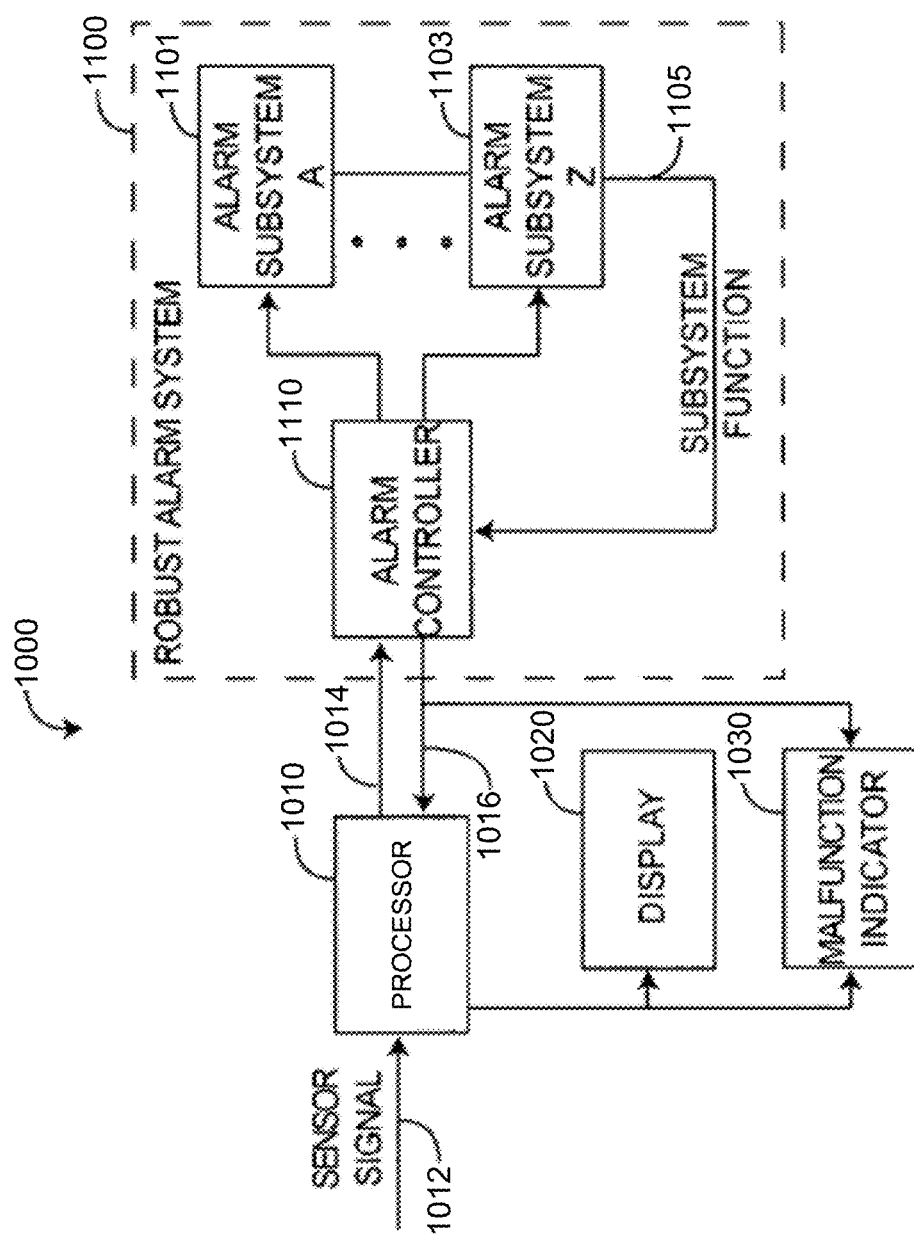
FIG. 10 depicts a more detailed example pulse oximetry system having a robust alarm system.

FIG. 10 illustrates a pulse oximetry system 1000 having a robust alarm system 1100. The pulse oximetry system 1000 has a hardware processor 1010 responsive to an input sensor signal 1012 and a display 1020 for presenting the results. For example, the processor 1010 may be part of a patient monitor that is responsive to an intensity signal from an optical sensor, such as the patient monitor 102 or 902 described above. The processor 1010 can have any of the characteristics of the processor 970 or other processors described herein. Unlike a conventional alarm, however, the robust alarm system 1100 can have redundant alarms and alarm system integrity checks, as described above and in additional detail below.

As shown in FIG. 10, the signal processor 1010 can input the sensor signal 1012 and generates an alarm trigger 1014 in response, such as when a parameter calculated by the signal processor is outside of predetermined limits. The alarm system 1100 inputs the alarm trigger signal 1014 and can activate one or more alarms accordingly, as described below. The alarm system 1100 can also output a malfunction signal 1016, which can indicate that one or more alarm subsystems 1101-1103 are unresponsive, for example are not generating an alarm in response to the alarm trigger 1014. The malfunction signal 1016 can be output to the signal processor 1010, which may trigger a malfunction indication on the display 1020 or trigger a separate malfunction indicator 1030, or both. The malfunction signal 1016 can also be output directly to the malfunction indicator 1030. The malfunction indicator 1030 may be an audible alert, visual alert or alert signal. An audible alert, for example, may be an alarm, buzzer, recorded or synthesized voice to name a few. A visual alert may be a flashing light or display message, for example. An alert signal may be, for instance, an electronic signal, code or message sent to another system via wired or wireless communication channels, or local area or wide area networks, to name a few.

Also shown in FIG. 10, the example robust alarm system 1100 has an alarm controller 1110 and one or more alarm subsystems 1101-1103. The alarm controller 1110 can input the alarm trigger 1110 and can activate an alarm subsystem 1101-1103 or multiple alarm subsystems concurrently. The alarm controller 1110 can also receive a subsystem function signal 1105 that provides feedback to the alarm controller 1110 as to the integrity of the alarm subsystems 1101-1103. The subsystem function signal 1105 can include circuit function signals 1132 (FIG. 11) or alarm function signals 1152 (FIG. 11) or both, as described with respect to FIG. 11, below.

The alarm controller 1110 can generate the malfunction signal 1016 if alarm subsystem integrity has been compromised. The malfunction signal 1016 can be encoded or otherwise configured so as to indicate a particular fault type or fault location or both. The fault location may be subsystem, component, or subcomponent specific. The alarm controller 1110 may activate or deactivate one or more alarm subsystems 1101-1103 in response to the subsystem function signal 1105 so as to work around one or more faulty alarm subsystems 1101-1103. In various embodiments, the alarm controller 1110 may include separate hardware, software, or firmware components or may be integrated with the signal processor 1010.

Further shown in FIG. 10, the robust alarm system 1100 can be configured for various self-testing, fault correction and alarm condition response. In monitors having two speakers instead of one, two or more alarm subsystems 1101-1103 can be concurrently activated so that multiple alarms sound simultaneously and so that failure of any one alarm or alarm subsystem 1101-1103 will not result in silence during an alarm condition. These multiple alarms may each sound at different frequencies or frequency spectra so as to facilitate alarm failure recognition and troubleshooting. The alarm controller 1110 can deactivate a failing alarm subsystem 1101-1103 and can activate one or more redundant alarm subsystems 1101-1103 in response to the subsystem function signal 1105. The alarm controller 1110 can also initiate alarm subsystem testing in the absence of an alarm condition by intermittently activating the alarm subsystems 1101-1103. Intermittent test alarms may be activated only long enough for subsystem function 1105 feedback or at frequencies outside of a normal hearing range so as to be essentially unnoticeable by caregivers, patients or other personnel operating the pulse oximetry system 1000.

Figure 11:
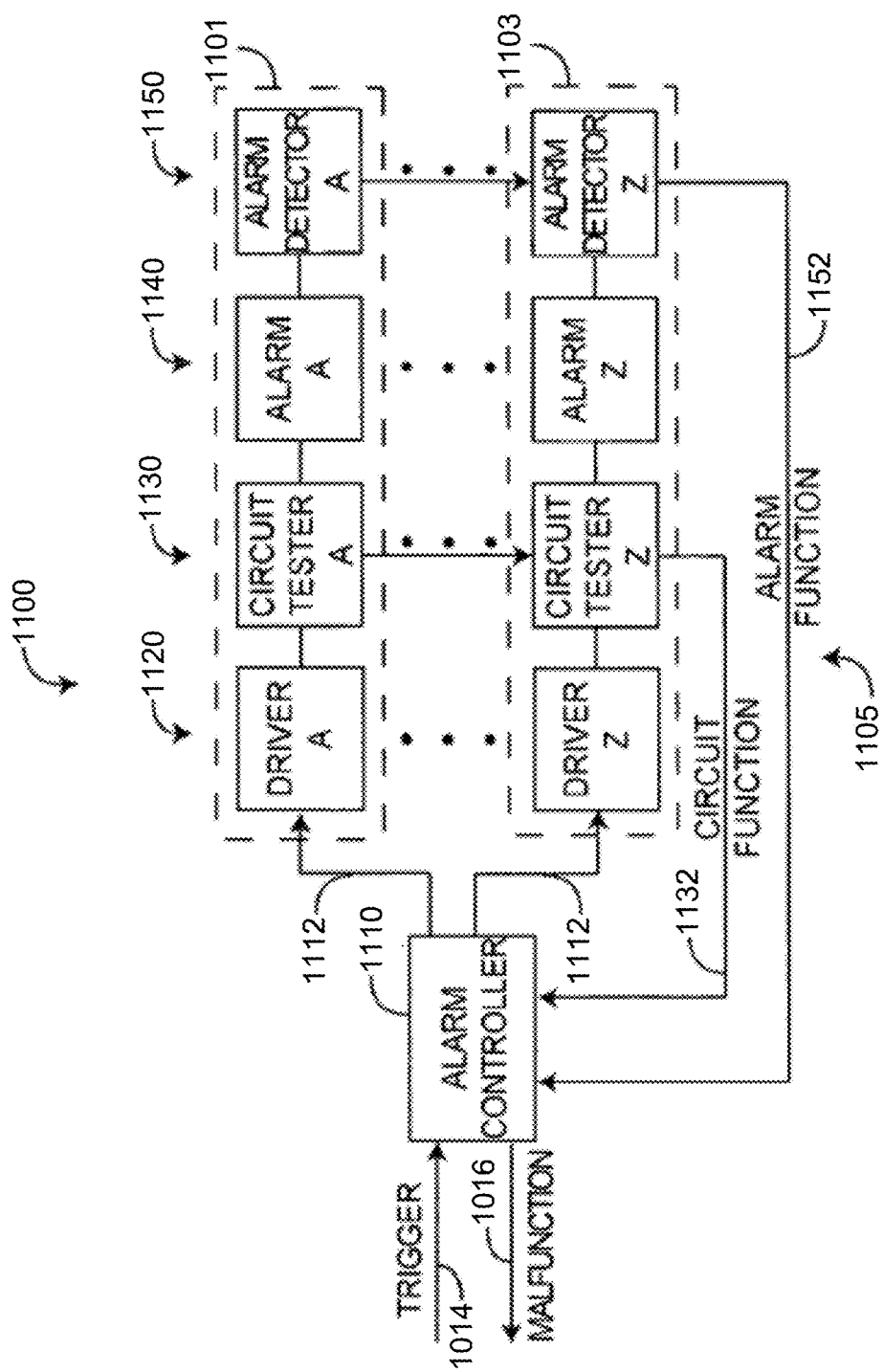
FIG. 11 depicts an example robust alarm system.

FIG. 11 illustrates a robust alarm system 1100 having an alarm controller 1110, drivers 1120, circuit testers 1130, alarms 1140 and detectors 1150. The robust alarm system 1100 is an example of the robust alarm system 1100 and 990. The alarm controller 1110 can respond to the alarm trigger 1014 (see FIG. 10) by outputting drive signals 1112 to one or more drivers 1120 so as to activate one or more of the alarms 1140. The alarms 1140 may be any of various audible transducers, such as speakers, piezoelectric transducers, buzzers or bells to name a few.

Also shown in FIG. 11, alarm detectors 1150 can interface with the alarms 1140 so as to verify the integrity of the alarm transducers. Alarm detectors 1150 can provide one or more alarm function signals 1152 to the alarm controller 1110, which the alarm controller 1110 can use to indicate and adapt to subsystem malfunctions, as described above.

Each alarm 1140 can have a corresponding alarm detector 1150 so that the alarm controller 1110 can identify a specific malfunctioning alarm. The robust alarm system 1100 may have one alarm detector 1150 for multiple alarms 1140 that each output a unique audio frequency or frequency spectrum so as to distinguish a malfunctioning alarm. The robust alarm system 1100 may have one alarm detector 1150 for all alarms 1140, where each alarm is sequentially and briefly activated during a periodic or intermittent testing procedure so as to determine the existence of any malfunctioning alarms.

A drive circuit integrity check can also be performed by the circuit testers 1130, as described in the '188 patent. A combination of a drive circuit integrity check and an alarm integrity check can increase overall alarm reliability.

Figure 12:
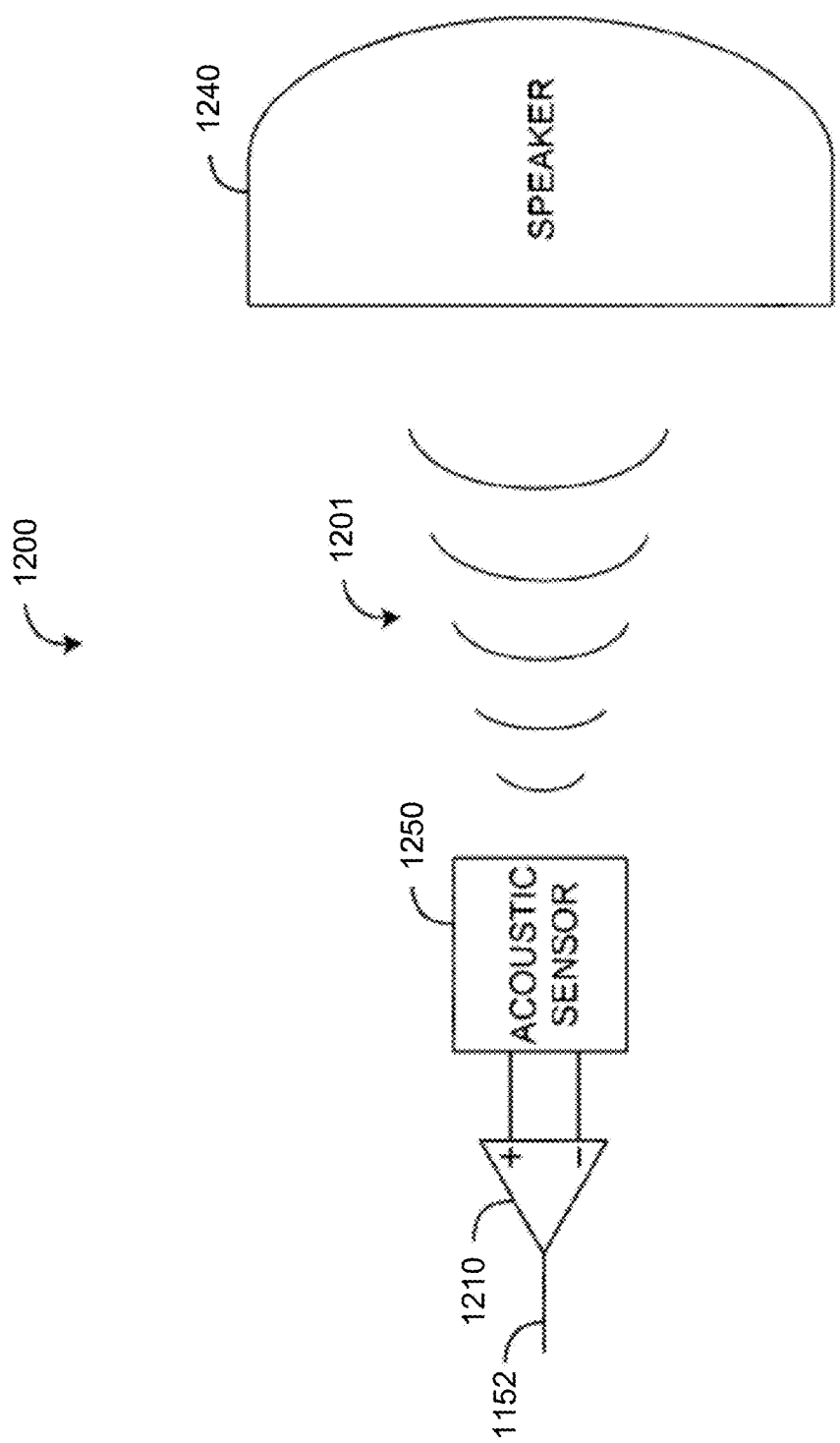
FIG. 12 depicts an example alarm detector.

FIG. 12 illustrates an example alarm detector 1150 (FIG. 11) that can verify alarm integrity. An acoustic sensor 1250, such as a microphone (see FIG. 1), can detect sound waves 1201 generated by the alarm transducer 1140 (FIG. 11), such as a loudspeaker (or speaker). An amplifier 1210 can generate a corresponding alarm function signal 1152 to the alarm controller 1110 (FIG. 11). If the alarm 1240 is operative, the alarm controller 1110 (FIG. 11) can detect a corresponding tone waveform in the alarm function signal 1152 upon activation of the drive signal 1112 (FIG. 11). Otherwise, an alarm malfunction can be determined, and the alarm controller 1110 (FIG. 11) can respond accordingly, such as by generating a malfunction signal 1016 (FIG. 11) or activating a redundant alarm 1140 (FIG. 11), or both.

V. Optional Medical Standards Implementation

Figure 13:
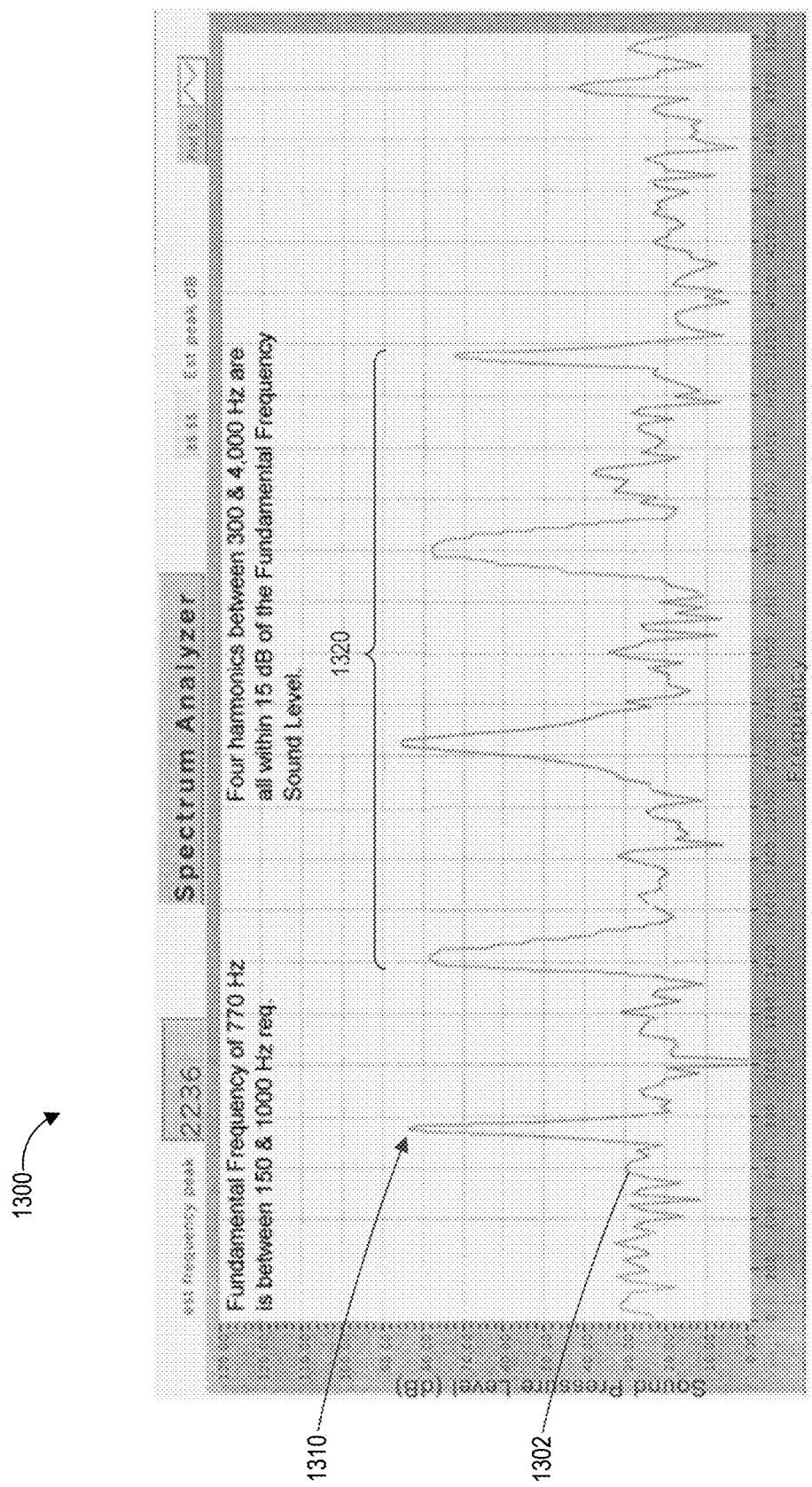
FIG. 13 depicts an example spectrum of an alarm signal.

FIG. 13 depicts an example spectrum 1300 of an alarm signal 1302 that may be used with any of the features described above. The spectrum 1300 is plotted according to frequency and sound pressure level (dB). The spectrum 1300 represents an example spectrum of a medical device alarm that comports with the voluntary standard defined in ANSI/AAMI/IEC 60601-1-8:2006 and A1:2012, "Medical Electrical Equipment—Part 1-8: General requirements for basic safety and essential performance-Collateral Standard: General requirements, tests and guidance for alarm systems in medical electrical equipment and medical electrical systems," issued 2006, which is hereby incorporated by reference in its entirety. An overview of the standard and the source of FIG. 13 is found in D. O'Brien, "Using Audible Alarms in Medical Equipment (IEC 60601-1-8), available from http://www.mallory-sonalert.com/Documents/Articles/Audible%20Alarms%20in%20Medical%20Equipment.pdf, last accessed on Apr. 17, 2018, which is hereby incorporated by reference in its entirety. IEC 60601-1-8 will first be described in general, and then with reference to FIG. 13. Example applications of IEC 60601-1-8 to the speaker analysis features described above will then be set forth.

IEC 60601-1-8 is a comprehensive international standard that specifies basic safety and performance requirements and tests for alarm systems in medical equipment. It covers numerous topics, from what kind of medical condition should trigger an audible warning sound to the specific frequency and shape of the audible sound waveform. The IEC 60601-1-8 standard is a voluntary standard, and thus in the context of this specification, it is viewed as an optional and not exclusive implementation of alarms that can be analyzed. Thus, any requirements of IEC 60601-1-8 should be viewed as optional to this disclosure.

IEC 60601-1-8 gives guidance on whether an alarm condition should be assigned a high, medium, or low priority. This guidance is based on the potential result of a failure to respond to the cause of the alarm condition and how fast the potential harm could happen to the patient. For example, a high priority would be assigned if death or irreversible injury could happen quickly, but a low priority would be assigned if only minor injury or discomfort may happen after a period of time.

IEC 60601-1-8 includes three burst requirements (again, all IEC "requirements" are optional herein). As this term is used herein, in addition to having its ordinary meaning, a burst can essentially include a pulse train of individual sounds (for example, beep, beep, beep, pause, beep, beep beep). The three burst requirements can correspond to the three priority conditions discussed in the last section. A high priority condition burst can have 10 fast pulses that repeat, a medium priority condition burst can have 3 slightly slower pulses that repeat, and a low priority condition burst can have 1 or 2 even slower pulses that may optionally repeat. The number of pulses, the shape of the pulse train, and the spacing of the pulses for each of the priority conditions are spelled out in detail in IEC 60601-1-8.

IEC 60601-1-8 requires that an individual sound pulse must have a fundamental frequency somewhere between 150 to 1000 Hz, and there must be at least four harmonic sounds from 300 to 4000 Hz. Again, these requirements are optional and may be varied in the context of this disclosure.

The spectrum 1300 of FIG. 13 shows a visible example of an audible sound that meets these requirements. The spectrum 1300 includes a peak 1310 to the far left, which is the fundamental frequency of the alarm sound, and four peaks 1320 to the right of the fundamental peaks that represent harmonics of the fundamental. To the ear, the resulting blended sound would be similar to hearing four different musical notes played at the same time. A final IEC 60601-1-8 requirement for the sound pulse characteristic is that the sound level (measured in dB) of the four harmonic tones (represented by peaks 1320) must be within +15 dB of the fundamental frequency tone. These requirements may be relaxed or varied in other implementations.

IEC 60601-1-8 also gives the option of providing more than one set of audible warning sounds that vary the fundamental frequency of the audible warning sound. What this means is that the equipment can play a musical melody instead of just beeping over and over with the same frequency sound. The sequence of musical notes for each melody can vary, but examples are spelled out for several different kinds of medical applications in the standard. For example, a ventilation alarm can be assigned one unique melody while a cardiac alarm can have a different unique melody. By assigning a unique melody for each kind of medical equipment, the possibility is that medical personnel can become familiar with each different kind of melody and more quickly identify the source of an audible warning sound.

The signal 1302 shown in FIG. 13 is a non-limiting example of a harmonic alarm that can be detected using the alarm analyzer 700 or 800 of FIG. 7 or 8. For example, the band-pass filters of the alarm analyzer 700 or 800 can have center frequencies at the frequencies of the fundamental peak 1310 and at each of the harmonic peaks 1320.

VI. Terminology

Many other variations than those described herein will be apparent from this disclosure. For example, depending on the embodiment, certain acts, events, or functions of any of the algorithms described herein can be performed in a different sequence, can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry that can process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "for example," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A patient monitor that measures a physiological parameter of a patient, the patient monitor comprising:
   a microphone;
   a loudspeaker;
   at least one physiological sensor; and
   a hardware processor that:
      receives a signal obtained from the at least one physiological sensor;
      determines a measurement value for the physiological parameter of the patient from the signal;
      determines that the measurement value triggers an alarm;
      outputs the alarm to the loudspeaker;
      after outputting the alarm to the loudspeaker, receives a microphone signal from the microphone;
      detects an audio signal indicative of the alarm in the microphone signal;
      determines that the audio signal indicative of the alarm is outside of an expected range;
      responsive to the determination that the audio signal indicative of the alarm is outside of the expected range, determines whether the loudspeaker is obstructed or malfunctioning;
      responsive to the determination that the loudspeaker is either obstructed or malfunctioning, determines that a volume of the alarm is insufficiently loud; and
      responsive to the determination that the volume of the alarm is insufficiently loud, outputs an error indication indicating that the loudspeaker is either obstructed or malfunctioning.

2. The patient monitor of claim 1, wherein the hardware processor detects a fundamental frequency of the audio signal indicative of the alarm.

3. The patient monitor of claim 2, wherein the hardware processor detects an absence of an expected frequency of the audio signal indicative of the alarm.

4. The patient monitor of claim 3, wherein after detecting the fundamental frequency and the absence of the expected frequency, the hardware processor determines the loudspeaker is malfunctioning.

5. The patient monitor of claim 1, wherein the hardware processor detects an expected frequency of the audio signal indicative of the alarm.

6. The patient monitor of claim 5, wherein the hardware processor detects an absence of a fundamental frequency of the audio signal indicative of the alarm.

7. The patient monitor of claim 6, wherein after detecting the expected frequency and the absence of the fundamental frequency of the audio signal indicative of the alarm, the hardware processor determines the loudspeaker is malfunctioning.

8. The patient monitor of claim 1, wherein the hardware processor detects a plurality of expected frequencies of the audio signal indicative of the alarm.

9. The patient monitor of claim 8, wherein the hardware processor determines that each peak of the plurality of expected frequencies is outside of the expected range.

10. The patient monitor of claim 9, wherein after determining each peak of the plurality of expected frequencies is outside of the expected range, the hardware processor determines the loudspeaker is obstructed.

11. The patient monitor of claim 9, wherein the hardware processor determines that each peak of the plurality of expected frequencies is above a predetermined threshold.

12. The patient monitor of claim 11, wherein the hardware processor determines a relative difference between peaks of the plurality of expected frequencies.

13. The patient monitor of claim 12, wherein after determining that each peak of the plurality of expected frequencies is above the predetermined threshold and determining a relative difference between peaks of the plurality of expected frequencies, the hardware processor determines the loudspeaker is obstructed.

14. A patient monitoring method comprising:
   under control of a patient monitor comprising a hardware processor:
      receiving a signal obtained from at least one physiological sensor;
      determining a measurement value for a physiological parameter of a patient from the signal;
      determining that the measurement value triggers an alarm;
      outputting the alarm to a loudspeaker;
      after outputting the alarm to the loudspeaker, receiving a microphone signal from a microphone;
      detecting an audio signal indicative of the alarm in the microphone signal;
      determining that the audio signal indicative of the alarm is outside of an expected range;
      responsive to determining that the audio signal indicative of the alarm is outside of the expected range, determining whether the loudspeaker is obstructed or malfunctioning;
      responsive to determining that the loudspeaker is either obstructed or malfunctioning, determining that a volume of the alarm is insufficiently loud; and
      responsive to determining that the volume of the alarm is insufficiently loud, outputting an error indication indicating that the loudspeaker is either obstructed or malfunctioning.

15. The patient monitoring method of claim 14, wherein the detecting of the audio signal indicative of the alarm comprises:
   detecting a fundamental frequency of the audio signal indicative of the alarm; and
   detecting an absence of an expected frequency of the audio signal indicative of the alarm.

16. The patient monitoring method of claim 15, wherein after detecting the fundamental frequency and the absence of the expected frequency of the audio signal indicative of the alarm, the determining of whether the loudspeaker is obstructed or malfunctioning comprises determining the loudspeaker is malfunctioning.

17. The patient monitoring method of claim 14, wherein detecting of the audio signal indicative of the alarm comprises:
   detecting an expected frequency of the audio signal indicative of the alarm; and
   detecting an absence of a fundamental frequency of the audio signal indicative of the alarm.

18. The patient monitoring method of claim 17, wherein after detecting the expected frequency and the absence of the fundamental frequency of the audio signal indicative of the alarm, the determining of whether the loudspeaker is obstructed or malfunctioning comprises determining the loudspeaker is malfunctioning.

19. The patient monitoring method of claim 14, wherein the detecting of the audio signal indicative of the alarm comprises detecting a plurality of expected frequencies of the audio signal indicative of the alarm; and wherein the determining of the audio signal indicative of the alarm outside of the expected range comprises determining that each peak of the plurality of expected frequencies is outside of the expected range.

20. The patient monitoring method of claim 19, wherein after determining each peak of the plurality of expected frequencies is outside of the expected range, the determining of whether the loudspeaker is obstructed or malfunctioning comprises determining the loudspeaker is obstructed.

21. The patient monitoring method of claim 19, wherein the determining that each peak of the plurality of expected frequencies is outside of the expected range comprises:

determining that each peak of the plurality of expected frequencies is above a predetermined threshold; and determining a relative difference between peaks of the plurality of expected frequencies.

22. The patient monitoring method of claim 21, wherein after determining that each peak of the plurality of expected frequencies is above the predetermined threshold and determining a relative difference between peaks of the plurality of expected frequencies, the determining of whether the loudspeaker is obstructed or malfunctioning comprises determining the loudspeaker is obstructed.

\* \* \* \* \*